United States Patent [19]

Sasaki et al.

[11] Patent Number: 5,808,024
[45] Date of Patent: Sep. 15, 1998

[54] NUCLEIC ACIDS ENCODING HIGH MOLECULAR WEIGHT MAJOR OUTER MEMBRANE PROTEIN OF MORAXELLA

[76] Inventors: Ken Sasaki, 1131 Steeles Avenue, West, Apt. No. 512, Willowdale, Ontario, Canada, M2R 3W8; Robin E. Harkness, 640 Sheppard Avenue, East, Apt. #1706, Willowdale, Ontario, Canada, M2K 1B8; Sheena M. Loosmore, 70 Crawford Rose Drive, Aurora, Ontario, Canada, L4G 4R4; Michel H. Klein, 16 Munro Boulevard, Willowdale, Ontario, Canada, M2P 1B9

[21] Appl. No.: 478,370

[22] Filed: Jun. 7, 1995

Related U.S. Application Data

[63] Continuation-in-part of Ser. No. 431,718, May 1, 1995.
[51] Int. Cl.$^6$ .................................................. C07H 21/02
[52] U.S. Cl. ...................... 536/23.1; 435/69.1; 435/69.7; 435/252.3; 435/320.1; 435/325; 530/300; 530/350; 536/23.5; 424/251.1
[58] Field of Search ................................ 435/69.1, 69.7, 435/252.3, 320.1; 530/300, 350; 536/23.1, 23.5; 424/251.1

[56] References Cited

U.S. PATENT DOCUMENTS

| | | | |
|---|---|---|---|
| 4,258,029 | 3/1981 | Moloney et al. | 424/49 |
| 4,855,283 | 8/1989 | Lockhoff et al. | 514/8 |

FOREIGN PATENT DOCUMENTS

| | | | |
|---|---|---|---|
| WO A 93 03761 | 3/1883 | WIPO . | |
| WO A 91 09952 | 7/1991 | WIPO . | |
| 9303761 | 3/1993 | WIPO . | |
| WO A 93 10214 | 5/1993 | WIPO . | |

OTHER PUBLICATIONS

Van Hare, G.F., P.A. Shurin, C.D. Marchant, N.A. Cartelli, C.E.Johnson, D. Fulton, S. Carlin, and C.H. Kim. Acute otitis media caused by *Branhamella catarrhalis*: biology and therapy. Rev. Infect. Dis. 9:16–27.

Chapman, A.J., D.M. Musher, S. Jonsson, J.E. Clarridge, and R.J. Wallace. 1985. Development of bactericidal antibody during *Branhamella catarrhalis* infection. J. Infect. Dis. 151:878–882.

Hager, H., A. Verghese, S. Alvarez, and S.L. Berk. 1987. *Branhamella catarrhalis* respiratory infections. Rev. Infect. Dis. 9:1140–1149.

McLeod, D.T., F. Ahmad, M.J. Croughan, and M.A. Calder. 1986. Bronchopulmonary infection due to *M. catarrhalis*. Clinical features and therapeutic response. Drugs 31(Suppl.3):109–112.

Nicotra, B., M. Rivera, J.I. Luman, and R.J. Wallace. 1986. *Branhamella catarrhalis* as a lower respiratory tract pathogen in patients with chronic lung disease. Arch.Intern.Med. 146:890–893.

Ninane, G., J. Joly, and M. Kraytman. 1978. Bronchopulmonary infection due to *Branhamella catarrhalis* 11 cases assessed by transtracheal puncture. Br.Med.Jr. 1:276–278.

Srinivasan, G., M.J. Raff, W.C. Templeton, S.J. Givens, R.C. Graves, and J.C. Mel. 1981. *Branhamella catarrhalis* pneumonia. Report of two cases and review of the literature. Am.Rev. Respir. Dis. 123:553–555.

West, M., S.L. Berk, and J.K. Smith. 1982. *Branhamella catarrhalis* pneumonia. South.Med. J. 75:1021–1023.

Brorson, J–E., A. Axelsson, and S.E. Holm. 1976. Studies on *Branhamelia catarrhalis* (*Neisseria catarrhalis*) with special reference to maxillary sinusitis. Scan. J. Infect. Dis. 8:151–155.

Evans, F.O., Jr., J.B. Sydnor, W.E.C. Moore, G.R. Moore, J.L. Manwaring, A.H. Brill, R.T. Jackson, S. Hanna, J.S. Skaar, L.V. Holdeman, G.S. Fitz–Hugh, M.A. Sande, and J.M. Gwaltney, Jr. 1975. Sinusitis of the maxillary antrum. N.Engl.J.Med. 293:735–739.

Tinkelman, D.G., and H.J. Silk. 1989. Clinical and bacteriologic features of chronic sinusitis in children. J.Pediatr. Am.J.Dis.Child. 143:938–942.

Wald, E.R., C. Byers, N.Guerra, M.Casselbrant, and D. Beste. 1989. Subacute sinusitis in children. J.Pediatr. 115:28–32.

Wald, E.R., G.J. Milmoe, A. Bowen, J.Ledesma–Medina, N. Salamon, and C.D.Bluestone. 1981. Acute maxillary sinusitis in children. N.Engl.J.Med. 304:749–754.

Christensen, J.J., and B. Bruun. 1985. Bacteremia caused by a beta–lactamase producing strain of *Branhamella catarrhalis*. Acta.Pathol. Microbiol. Immunol. Scand. Sect.B 93:273–275.

Craig, D.B., and P.A. Wehrle. 1983. *Branhamella catarrhalis* septic arthritis. J. Rheumatol. 10:985–986.

Gray, L.D., R.E. Van Scoy, J.P. Anhalt, and P.K.W. Yu. 1989. Wound infection caused by *Branhamella catarrhalis*. J.Clin.Microbiol. 27:818–820.

Guthrie, R., K. Bakenhaster, R.Nelson, and R. Woskobnick. 1988. *Branhamella catarrhalis* sepsis: a case report and review of the literature. J.Infect.Dis. 158:907–908.

Hiroshi, S., E.J. Anaissie, N.Khardori, and G.P. Bodey. 1988. *Branhamella catarrhalis* septicemia in patients with leukemia. Cancer 61:2315–2317.

(List continued on next page.)

*Primary Examiner*—Stephen Walsh
*Assistant Examiner*—Kenneth A. Sorensen

[57] ABSTRACT

An isolated and purified outer membrane protein of a Moraxella strain, particularly *M. catarrhalis*, has a molecular mass of about 200 kDa. The about 200 kDa outer membrane protein as well as nucleic acid molecules encoding the same are useful in diagnostic applications and immunogenic compositions, particularly for in vivo administration to a host to confer protection against disease caused by a bacterial pathogen that produces the about 200 kDa outer membrane protein or produces a protein capable of inducing antibodies in a host specifically reactive with the about 200 kDa outer membrane protein.

13 Claims, 17 Drawing Sheets

OTHER PUBLICATIONS

O'Neill, J.H., and P.W. Mathieson. 1987. Meningitis due to *Branhamella catarrhalis*. Aust. N.Z. J. Med. 17:241–242.

Murphy, T.F. 1989. The surface of *Branhamella catarrhalis*: a systematic approach to the surface antigens of an emerging pathogen. Pediatr. Infect. Dis. J. 8:S75–S77.

Klingman, K.L., and T.F. Murphy. 1994. Purification and characterization of a high–molecular–weight outer membrane protein of *Moraxella* (*Branhamella*) *catarrhalis*. Infect. Immun. 62:1150–1155.

Helminen, M.E., I. Maciver, J.L. Latimer, J. Klesney–Tait, L.D. Cope, M. Paris, G.H. McCracken, Jr., and E.J. Hansen. 1994. A large, antigenically conserved protein on the surface of *Moraxella catarrhalis* is a target for protective antibodies. J. Infect. Dis. 170:867–872.

Panezutti H., O. James, E.J. Hanson, Y. Choi, R.E. Harkness, M.H. Klein and P. Chong, 1993. Identification of surface–exposed B–cell epitopes recognized by *Haemophillus influenzae* type b P1 specific monoclonal antibodies. Infec. Immun. 61: 1867–1872.

Nixon–George et al. (1990), J. Immunology 144:4796–4802.

Wiesmuller (1989), Vaccine 8:29–33.

Deres et al. (1989), Nature 342:561.

Lockhoff, O. Glycolipids as Immunomodulators: Synthesis and Properties. 1991. Chem. Int. Ed. Engl. 30:1611–1620.

Journal of Infectious Diseases, 158 (4). 1988. 761–765., XP002013102 Bartos L C et al; "Comparison of the Outer Membrane Proteins of 50 Strains of *Branhamella–catarrhalis*" see the whole document.

Science, Apr. 14, 1995, 268 (5208) P221–5, United States, XP002013103 Casey PJ: "Protein lipidation in cell signaling." see the whole document.

Ostle et al. (1986) Am. J. Vet. Res 47:1415–142.

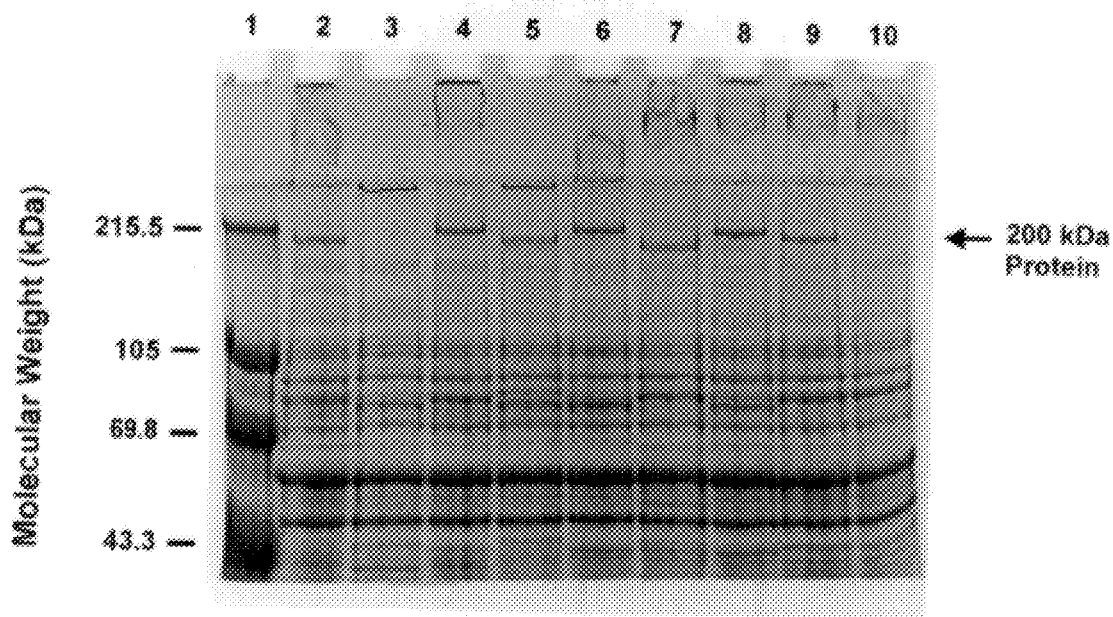

FIG. 6A

Nucleotide Sequence Between SalI and NcoI

```
         10         20         30         40         50         60         70
CCATGGATAT GGGCAGGTGT GCTCGCCTGC CGTATGATGG CGATGACACC CCATTTGCCC CATATCTGTA
         80         90        100        110        120        130        140
CGATTTGACA TGTGATATGA TTTAACATGT GACATGATTT AACATTGTTT AATACTGTTG CCATCATTAC
        150        160        170        180        190        200        210
CATAATTTAG TAACGCATTT AGTAACGCAT TTGTAAAAAT CATTGCGCCC CTTTATGTGT ATCATATGAA
        220        230        240        250        260        270        280
TAGAATATTA TGATTGTATC TGATTATTGT ATCAGAATGG TGATGCTATA TGATGATGCC TACGAGTTGA
        290        300        310        320        330        340        350
TTTGGGTTAA TCACTCTATG ATTTGATATA TTTTGAAACT AATCTATTGA CTTAAATCAC CATATGGTTA
        360        370        380        390        400        410        420
TAATTAGCA TAATGGTAGG CTTTTTGTAA AAATCACATC GCAATATTGT TCTACTGTTA CTACCATGCT
        430        440        450        460        470        480        490
TGAATGACGA TCCCAATCAC CAGATTCATT CAAGTGATGT GTTTGTATAC GCACCATTTA CCCTAATTAT
        500        510        520        530        540        550        560
TTCAATCAAA TGCCTATGTC AGCATGTATC ATTTTTTTAA GGTAAACCAC CATGAATCAC ATCTATAAAG
        570        580        590        600        610        620        630
TCATCTTTAA CAAAGCCACA GGCACATTTA TGGCAGTGGC AGAGTACGCC AAATCCCACA GCACGGGGGG
```

FIG.6B

```
       640         650         660         670         680         690         700
GGGTAGCTG   TGCTACAGGG  CAAGTTGGCA  GTGTATGCAC  TCTGAGCTTT  GCCCGTATTG  CCGCGCTCGC 710         720         730         740         750         760         770
TGTCCCTCGTG ATCGGTGCAA  CGCTCAGTGG  CAGTGCTTAT  GCTCAAAAAA  AAGATACCAA  ACATATCGCA 780         790         800         810         820         830         840
ATTGGTGAAC  AAAACCAGCC  AAGACGCTCA  GGCACTGCCA  AGGCGGACGG  TGATCGAGCC  ATTGCTATTG 850         860         870         880         890         900         910
GTGAAAATGC  TAACGCACAG  GGCGGTCAAG  CCATCGCCAT  CGGTAGTAGT  AATAAAACTG  TCAATGGAAG 920         930         940         950         960         970         980
CAGTTTGGAT  AAGATAGGTA  CCGATGCTAC  GGGTCAAGAG  TCCATCGCCA  TCGGTGGTGA  TGTAAAGGCT 990         1000        1010        1020        1030        1040        1050
AGTGGTGANG  CCTCGATTGC  CATCGGTAGT  GATGACTTAC  ATTTGCTTGA  TCAGCATGGT  AATCCTAAAC 1060        1070        1080        1090        1100        1110        1120
ATCCGAAAGG  TACTCTGATT  AACGATCTTA  TTAACGGCCA  TGCAGTATTA  AAAGAAATAC  GAAGCTCAAA 1130        1140        1150        1160        1170        1180        1190
GGATAATGAT  GTAAAATATA  GACGCACAAC  CGCAAGCGGA  CACGCCAGTA  CTGCAGTGGG  AGCCATGTCA 1200        1210        1220        1230        1240        1250        1260
TATGCACAGG  GTCATTTTTC  CAACGCCTTT  GGTACACGGG  CAACAGCTAA  AAGTGCCTAT  TCCTTGGCAG
```

FIG. 6C

```
   1270        1280        1290        1300        1310        1320        1330
TGGGTCTTGC  CGCCACAGCC  GAGGGCCAAT  CTACAATCGC  TATTGGTTCT  GATGCAACAT  CTAGCTCGTT 1340        1350        1360        1370        1380        1390        1400
GGGAGCGATA  GCCCTTGGTG  CAGGTACTCG  TGCTCAGCTA  CAGGGCAGTA  TTGCCCTAGG  TCAAGTTCT 1410        1420        1430        1440        1450        1460        1470
GTTGTCACTC  AGAGTGATAA  TAATTCTAGA  CCGGCCTATA  CACCAAATAC  CCAGGCACTA  GACCCCAAGT 1480        1490        1500        1510        1520        1530        1540
TTCAAGCCAC  CAATAATACG  AAGGCGGGTC  CACTTTCCAT  TGGTAGTAAC  TCTATCAAAC  GTAAAATCAT 1550        1560        1570        1580        1590        1600        1610
CAATGTCGGT  GCAGGTGTTA  ATAAAACCGA  TGCGGTCAAT  GTGGCACAGC  TAGAAGCGGT  GGTGAAGTGG 1620        1630        1640        1650        1660        1670        1680
GCTAAGGAGC  GTAGAATTAC  TTTTCAGGGT  GATGATAACA  GTACTGACGT  AAAAATAGGT  TTGGATAATA 1690        1700        1710        1720        1730        1740        1750
CTTTAACTAT  TAAAGGTGGT  GCAGAGACCA  ACGCATTAAC  CGATAATAAT  ATCGGTGTGG  TAAAAGAGGC 1760        1770        1780        1790        1800        1810        1820
TGATAATAGT  GGTCTGAAAG  TTAAACTTGC  TAAAACTTTA  AACAATCTTA  CTGAGGTGAA  TACAACTACA 1830        1840        1850        1860        1870        1880        1890
TTAAATGCCA  CAACCACAGT  TAAGGTAGGT  AGTAGTAGTA  GTACTACAGC  TGAATTATTG  AGTGATAGTT
```

FIG.6D

| | | | | | | |
|---|---|---|---|---|---|---|
| 1900<br>TAACCTTTAC | 1910<br>CCAGCCCAAT | 1920<br>ACAGGCAGTC | 1930<br>AAAGCACAAG | 1940<br>CAAAACCGTC | 1950<br>TATGGCGTTA | 1960<br>ATGGGGTGAA |
| 1970<br>GTTTACTAAT | 1980<br>AATGCAGAAA | 1990<br>CAACAGCAGC | 2000<br>AATCGGCACT | 2010<br>ACTCGTATTA | 2020<br>CCAGAGATAA | 2030<br>AATTGGCTTT |
| 2040<br>GCTCGAGATG | 2050<br>GTGATGTTGA | 2060<br>TGAAAAACAA | 2070<br>GCACCATATT | 2080<br>TGGATAAAAA | 2090<br>ACAACTTAAA | 2100<br>GTGGGTAGTG |
| 2110<br>TTGCAATTAC | 2120<br>CATAGACAAT | 2130<br>GGCATTGATG | 2140<br>CAGGTAATAA | 2150<br>AAAGATCAGT | 2160<br>AATCTTGCCA | 2170<br>AAGGTAGCAG |
| 2180<br>TGCTAACGAT | 2190<br>GCGGTTACCA | 2200<br>TCGAACAGCT | 2210<br>CAAAGCCGCC | 2220<br>AAGCCTACTT | 2230<br>TAAACGCAGG | 2240<br>CGCTGGCATC |
| 2250<br>AGTGTCACAC | 2260<br>CTACTGAAAT | 2270<br>ATCAGTTGAT | 2280<br>GCTAAGAGTG | 2290<br>GCAATGTTAC | 2300<br>CGCCCCAACT | 2310<br>TACAACATTG |
| 2320<br>GCGTGAAAAC | 2330<br>CACCGAGCTT | 2340<br>AACAGTGATG | 2350<br>GCACTAGTGA | 2360<br>TAAATTTAGT | 2370<br>GTTAAGGGTA | 2380<br>GTGGTACGAA |
| 2390<br>CAATAGCTTA | 2400<br>GTTACCGCCG | 2410<br>AACATTTGGC | 2420<br>AAGCTATCTA | 2430<br>AATGAAGTCA | 2440<br>ATCGAACGGC | 2450<br>TGACAGTGCT |
| 2460<br>CTACAAAGCT | 2470<br>TTACCGTTAA | 2480<br>AGAAGAAGAC | 2490<br>GATGATGACG | 2500<br>CCAACGCTAT | 2510<br>CACCGTGGCT | 2520<br>AAAGATACGA |

FIG.6E

```
2530       2540       2550       2560       2570       2580       2590
CAAAAAATGC CGGCGCAGTC AGCATCTTAA AACTCAAAGG TAAAAACGGT CTAACGGTTG CTACCAAAAA
2600       2610       2620       2630       2640       2650       2660
AGATGGTACG GTTACCTTTG GGCTTAGCCA AGATAGCGGT CTGACCATTG GCAAAAGCAC CCTAAACAAC
2670       2680       2690       2700       2710       2720       2730
GATGGCTTGA CTGTTAAAGA TACCAACGAA CAAATCCAAG TCGGTGCTAA TGGCATTAAA TTTACTAATG
2740       2750       2760       2770       2780       2790       2800
TGAATGGTAG TAATCCAGGT ACTGGCATTG CAAATACCGC AGAGATAAAA TTGGCTTTGC
2810       2820       2830       2840       2850       2860       2870
TGGTTCTGAT GGTGCAGTTG ATACAAACAA ACCTTATCTT GATCAAGACA AGCTACAAGT TGGCAATGTT
2880       2890       2900       2910       2920       2930       2940
AAGATTACCA ACACTGGCAT TAACGCAGGT GGTAAAGCCA TCACAGGGCT GTCCCCAACA CTGCCTAGCA
2950       2960       2970       2980       2990       3000       3010
TTGCCGATCA AAGTAGCCGC AACATAGAAC TGGGCAATAC AATCCAAGAC AAAGACAAAT CCAACGCTGC
3020       3030       3040       3050       3060       3070       3080
CAGCATTAAT GATATATTAA ATACAGGCTT TAACCTAAAA AATAATAACA ACCCCATTGA CTTTGTCTCC
3090       3100       3110       3120       3130       3140       3150
ACTTATGACA TTGTTGACTT TGCCAATGGC AATGCCACCA CCGCCACAGT AACCCATGAT ACCGCTAACA
```

FIG.6F

```
       3160                 3170                 3180                 3190                 3200                 3210                 3220
AAACCAGTAA           AGTGGTATAT           GATGTGAATG           TGGATGATAC           AACCATTCAT           CTAACAGGCA           CTGATGACAA 3230                 3240                 3250                 3260                 3270                 3280                 3290
TAAAAAACTT           GGCGTCAAAA           CCACCAAACT           GAACAAAACA           AGTGCTAATG           GTAATACAGC           AACTAACTTT 3300                 3310                 3320                 3330                 3340                 3350                 3360
AATGTTAACT           CTAGTGATGA           AGATGCCCTT           GTTAACGCCA           AAGACATCGC           CGAAAATCTA           AACACCCTAG 3370                 3380                 3390                 3400                 3410                 3420                 3430
CCAAGGAAAT           TCACACCACC           AAAGGCACAG           CAGACACCGC           CCTACAAACC           TTTACCGTTA           AAAAGGTAGA 3440                 3450                 3460                 3470                 3480                 3490                 3500
TGAAAATAAT           AATGCTGATG           ACGCCAACGC           CATCACCGTG           GGTCAAAAGA           ACGCAAATAA           TCAAGTCAAC 3510                 3520                 3530                 3540                 3550                 3560                 3570
ACCCTAACAC           TCAAAGGTGA           AAACGGTCTT           AATATTAAAA           CCGACAAAAA           TGGTACGGTT           ACCTTTGGCA 3580                 3590                 3600                 3610                 3620                 3630                 3640
TTAACACCAC           AAGCGGTCTT           AAAGCCCGGCA           AAAGCACCCT           AAACGACGGT           GGCTTGTCTA           TTAAAAACCC 3650                 3660                 3670                 3680                 3690                 3700                 3710
CACTGGTAGC           GAACAAATCC           AAGTCGGTGC           TGATGGCGTG           AAGTTTGCCA           AGGTTAATAA           TAATGGTGTT 3720                 3730                 3740                 3750                 3760                 3770                 3780
GTAGGTGCTG           GCATTGATGG           CACAACTCGC           ATTACCAGAG           ATGAAATTGG           CTTTACTGGG           ACTAATGGCT
```

FIG.6G

```
      3790       3800       3810       3820       3830       3840       3850
CACTTGATAA AAGCAAACCC CACCTAAGCA AAGACGGCAT TAACGCAGGT GGTAAAAAGA TTACCAACAT 3860       3870       3880       3890       3900       3910       3920
TCAATCAGGT GAGATTGCCC AAAACAGCCA TGATGCTGTG ACAGGCGGCA AGATTTATGA TTTAAAAACC 3930       3940       3950       3960       3970       3980       3990
GAACTTGAAA ACAAAATCAG CAGTACTGCC AAAACAGCAC AAAACTCATT ACACGAATTC TCAGTAGCAG 4000       4010       4020       4030       4040       4050       4060
ATGAACAAGG TAATAACTTT ACGGTTAGTA ACCCTTACTC CAGTTATGAC ACCTCAAAGA CCTCTGATGT 4070       4080       4090       4100       4110       4120       4130
CATCACCTTT GCAGGTGAAA ACGGCATTAC CACCAAGGTA AATAAAGGTG TGGTGCGTGT GGGCATTGAC 4140       4150       4160       4170       4180       4190       4200
CAAACCAAAG GCTTAACCAC GCCTAAGCTG ACCGTGGGTA ATAATAATGG CAAAGGCATT GTCATTGACA 4210       4220       4230       4240       4250       4260       4270
GCCAAAATGG TCAAATACC  ATCACAGGAC TAAGCAACAC TCTAGCTAAT GTTACCAATG ATAAAGGTAG 4280       4290       4300       4310       4320       4330       4340
CGTACGCACC ACAGAACAGG GCAATATAAT CAAAGACGAA GACAAAACCC GTGCCGCCAG CATTGTTGAT 4350       4360       4370       4380       4390       4400       4410
GTGCTAAGCG CAGGCTTTAA CTTGCAAGGC AATGGTGAAG CGGTTGACTT TGTCTCCACT TATGACACCG
```

FIG.6H

```
        4420       4430       4440       4450       4460       4470       4480
  TCAACTTTGC CGATGGCAAT GCCACCACCG CTAAGGTGAC CTATGATGAC ACAAGCAAAA CCAGTAAAGT
        4490       4500       4510       4520       4530       4540       4550
  GGTCTATGAT GTCAATGTGG ATGATACAAC CATTGAAGTT AAAGATAAAA AACTTGGCGT AAAAACCACC
        4560       4570       4580       4590       4600       4610       4620
  ACATTGACCA GTACTGGCAC AGGTGCTAAT AAATTTGCCC TAAGCAATCA AGCTACTGGC GATGCGCTTG
        4630       4640       4650       4660       4670       4680       4690
  TCAAGGCCAG TGATATCGTT GCTCATCTAA ACACCTTATC TGGCGACATC CAAACTGCCA AAGGGGCAAG
        4700       4710       4720       4730       4740       4750       4760
  CCAAGCGAAC AACTCAGCAG GCTATGTGGA TGCTGATGGC AATAAGGTCA TCTATGACAG TACCGATAAC
        4770       4780       4790       4800       4810       4820       4830
  AAGTACTATC AAGCCAAAAA TGATGGCACA GTTGATAAAA CCAAAGAAGT TGCCAAAGAC AAACTGGTCG
        4840       4850       4860       4870       4880       4890       4900
  CCCAAGCCCA AACCCCAGAT GGCACATTGG CTCAAATGAA TGTCAAATCA GTCATTAACA AAGAACAAGT
        4910       4920       4930       4940       4950       4960       4970
  AAATGATGCC AATAAAAAGC AAGGCATCAA TGAAGACAAC GCCTTTGTTA AAGGACTTGA AAAAGCCGCT
        4980       4990       5000       5010       5020       5030       5040
  TCTGATAACA AAACCAAAAA CGCCGCAGTA ACTGTGGGTG ATTTAAATGC CGTTGCCCAA ACACCGCTGA
```

FIG. 6I

```
5050       5060       5070       5080       5090       5100       5110
CCTTTGCAGG GGATACAGGC ACAACGGCTA AAAAACTGGG CGAGACTTTG ACCATCAAAG GTGGGCAAAC 5120       5130       5140       5150       5160       5170       5180
AGACACCAAT AAGCTAACCG ATAATAACAT CGGTGTGGTA GCAGGTACTG ATGGCTTCAC TGTCAAACTT 5190       5200       5210       5220       5230       5240       5250
GCCAAAGACC TAACCAATCT TAACAGCGTT AATGCAGGTG GCACCAAAAT TGATGACAAA GGCGTGTCTT 5260       5270       5280       5290       5300       5310       5320
TTGTAGACTC AAGCGGTCAA GCCAAAGCAA ACACCCCTGT GCTAAGTGCC AATGGGCTGG ACCTGGGTGG 5330       5340       5350       5360       5370       5380       5390
CAAGGTCATC AGTAATGTGG GCAAAGGCAC AAAAGATACC ATGTACAACA GTTAAACGAA 5400       5410       5420       5430       5440       5450       5460
GTACGCAACT TGTTGGGTCT TGGTAATGCT ACGCTGACGG CAATCAGGTA AACATTGCCG 5470       5480       5490       5500       5510       5520       5530
ACATCAAAAA AGACCCAAAT TCAGGTTCAT GGTAATGATA CATCTAACCG CACTGTCATC AAAGCAGGCA CGGTACTTGG 5540       5550       5560       5570       5580       5590       5600
CGGTAAAGGT AATAACGATA CCGAAAAACT TGCCACTGGT GGTATACAAG TGGGCGTGGA TAAAGACGGC 5610       5620       5630       5640       5650       5660       5670
AACGCTAACG GCGATTTAAG CAATGTTTGG GTCAAAACCC AAAAAGATGG CAGCAAAAAA GCCCTGCTCG 5680       5690       5700       5710       5720       5730       5740
CCACTTATAA CGCCGCAGGT CAGACCAACT ATTTGACCAA CAACCCCGCA GAAGCCATTG ACAGAATAAA
```

FIG.6J

```
5750 TGAACAAGGT ATCCGCTTCT TCCATGTCAA CGATGGCAAT CAAGAGCCTG TGGTACAAGG GCGTAACGGC 5810
5820 ATTGACTCAA GTGCCCTCAGG CAAGCACTCA GTGGCGATAG GTTTCCAGGC CAAGGCAGAT GGTGAAGCCG 5880
5890 CCGTTGCCAT AGGCAGACAA ACCCAAGCAG GCAACCAATC CATCGCCATC GGTGATAACG CACAAGCCAC 5950
5960 GGGCGATCAA TCCATCGCCA TCGGTACAGG CAATGTGGTA GCAGGTAAGC ACTCTGGTGC CATCGGCGAC 6020
6030 CCAAGCACTG TTAAGGCTGA TAACAGTTAC AGTGTGGGTA ATAACAACCA GTTTACCGAT GCCACTCAAA 6090
6100 CCGATGTCTT TGGTGTGGGC AATAACATCA CCGTGACCGA AAGTAACTCG GTTGCCTTAG GTTCAAACTC 6160
6170 TGCCATCAGT GCAGGCACAC ACGCAGGCAC ACAAGCCAAA AAATCTGACG GCACAGCAGG GTTGCCTTAG 6230
6240 ACAGCAGGTG CAACCGGTAC GGTTAAAGGC TTTGCTGGAC ACAAGCCAAA AAACGGCGGT TGGTGCGGGT TCCGTGGGTG 6300
6310 CCTCAGGTGC TGAACGCCGT ATCCAAAATG TGGCAGCAGG TGAGGTCAGT GCCACCAGCA CCGATGCGGT 6370
6380 CAATGGTAGC CAGTTGTACA AAGCCACCCA AAGCATTGCC AACGCAACCA ATGAGCTTGA CCATCGTATC 6440
```

FIG.6K

| | | | | | | |
|---|---|---|---|---|---|---|
| 6450 | 6460 | 6470 | 6480 | 6490 | 6500 | 6510 |
| CACCAAAACG | AAAATAAGGC | CAATGCAGGG | ATTTCATCAG | CGATGGCGAT | GGCGTCCATG | CCACAAGCCT |
| 6520 | 6530 | 6540 | 6550 | 6560 | 6570 | 6580 |
| ACATTCCTGG | CAGATCCATG | GTTACCGGGG | GTATTGCCAC | CCACAACGGT | CAAGGTGCGG | TGGCAGTGGG |
| 6590 | 6600 | 6610 | 6620 | 6630 | 6640 | 6650 |
| ACTGTCGAAG | CTGTCGGATA | ATGGTCAATG | GGTATTTAAA | ATCAATGGTT | CAGCCGATAC | CCAAGGCCAT |
| 6660 | 6670 | 6680 | 6690 | 6700 | 6710 | 6720 |
| GTAGGGGCGG | CAGTTGGTGC | AGGTTTTCAC | TTTTAAGCCA | TAAATCGCAA | GATTTTACTT | AAAAATCAAT |
| 6730 | 6740 | 6750 | 6760 | 6770 | 6780 | 6790 |
| CTCACCATAG | TTGTATAAAA | CAGCATCAGC | ATCAGTCATA | TTACTGATGC | TGATGTTTTT | TATCACTTAA |
| 6800 | 6810 | 6820 | 6830 | 6840 | 6850 | 6860 |
| ACCATTTTAC | CGCTCAAGTG | ATTCTCTTTC | ACCATGACCA | AATCGCCATT | GATCATAGGT | AAACTTATTG |
| 6870 | 6880 | 6890 | 6900 | 6910 | 6920 | 6930 |
| AGTAAATTTT | ATCAATGTAG | TTGTTAGATA | TGGTTAAAAT | TGTGCCATTG | ACCAAAAAAT | GACCGATTTA |
| 6940 | 6950 | 6960 | 6970 | | | |
| TCCCGAAAAT | TTCTGATTAT | GATCCGTTGA | CCTGCAGGTC | GAC | | |

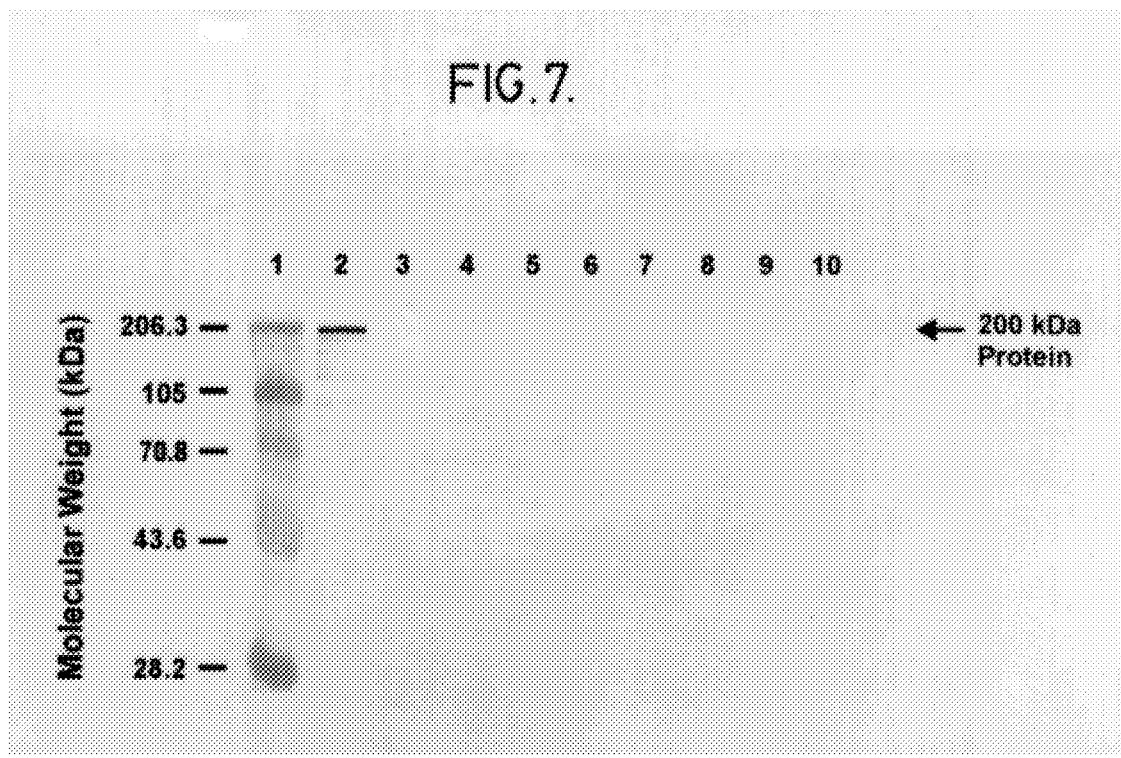

NUCLEIC ACIDS ENCODING HIGH MOLECULAR WEIGHT MAJOR OUTER MEMBRANE PROTEIN OF MORAXELLA

REFERENCE TO RELATED APPLICATION

This application is a continuation-in-part of copending U.S. patent application Ser. No. 08/431,718 filed May 1, 1995.

FIELD OF THE INVENTION

The present invention relates to the field of immunology and is particularly concerned with outer membrane proteins from Moraxella, methods of production thereof, genes encoding such proteins and uses thereof.

BACKGROUND OF THE INVENTION

Otitis media is the most common illness of early childhood with approximately 70% of all children suffering at least one bout of otitis media before the age of seven. Chronic otitis media can lead to hearing, speech and cognitive impairment in children. It is caused by bacterial infection with *Streptococcus pneumoniae* (approximately 50%), non-typable *Haemophilus influenzae* (approximately 30%) and *Moraxella* (*Branhamella*) *catarrhalis* (approximately 20%). In the United States alone, treatment of otitis media costs between one and two billion dollars per year for antibiotics and surgical procedures, such as tonsillectomies, adenoidectomies and insertion of tympanostomy tubes. Because otitis media occurs at a time in life when language skills are developing at a rapid pace, developmental disabilities specifically related to learning and auditory perception have been documented in youngsters with frequent otitis media.

*M. catarrhalis* mainly colonizes the respiratory tract and is predominantly a mucosal pathogen. Studies using cultures of middle ear fluid obtained by tympanocentesis have shown that *M. catarrhalis* causes approximately 20% of cases of otitis media (ref. 1—Throughout this application, various references are referred to in parenthesis to more fully describe the state of the art to which this invention pertains. Full bibliographic information for each citation is found at the end of the specification, immediately preceding the claims. The disclosures of these references are hereby incorporated by reference into the present disclosure).

The incidence of otitis media caused by *M. catarrhalis* is increasing. As ways of preventing otitis media caused by pneumococcus and nontypeable *H. influenzae* are developed, the relative importance of *M. catarrhalis* as a cause of otitis media can be expected to further increase.

*M. catarrhalis* is also an important cause of lower respiratory tract infections in adults, particularly in the setting of chronic bronchitis and emphysema (refs. 2, 3, 4, 5, 6, 7, and 8). *M. catarrhalis* also causes sinusitis in children and adults (refs. 9, 10. 11, 12, and 13) and occasionally causes invasive disease (refs. 14, 15, 16, 17, 18, and 19).

Like other Gram-negative bacteria, the outer membrane of *M. catarrhalis* consists of phospholipids, lipopolysaccharide (LPS), and outer membrane proteins (OMPs). Eight of the *M. catarrhalis* OMPs have been identified as major components. These are designated by letters A through H, beginning with OMP A which has a molecular mass of 98 kDa to OMP H which has a molecular mass of 21 kDa (ref. 20).

Recently, a high-molecular-weight outer membrane protein of *M. catarrhalis* was purified and characterized (ref. 21). The apparent molecular mass of this protein varies from 350 kDa to 720 kDa as judged by sodium dodecyl sulfate-polyacrylamide gel electrophoresis (SDS-PAGE). This protein appears to be an oligomer of much smaller proteins or subunits thereof of molecular mass 120 to 140 kDa and is antigenically conserved among strains of Moraxella.

A similar protein named UspA was also reported to be present on the surface of this species of bacteria with an apparent molecular mass of 300 to 400 kDa (ref. 22). Judging from the molecular mass, these two proteins may be the same.

*M. catarrhalis* infection may lead to serious disease. It would be advantageous to provide other outer membrane proteins for *M. catarrhalis* and genes encoding such proteins for use as antigens in immunogenic preparations including vaccines, carriers for other antigens and immunogens and the generation of diagnostic reagents.

SUMMARY OF THE INVENTION

The present invention is directed towards the provision of purified and isolated major outer membrane protein of *Moraxella catarrhalis* and other Moraxella strains, having an apparent molecular mass of about 200 kDa.

In accordance with one aspect of the invention, there is provided an isolated and purified, outer membrane protein of a Moraxella strain having a molecular weight of about 200 kDa, as determined by SDS-PAGE, or a fragment or an analog thereof. The outer membrane protein may be substantially in its native conformation (so as to have substantially retained the characteristic immunogenicity of the outer membrane protein in the Moraxella strain) and may be isolated from a *M. catarrhalis* strain, such as from *M. catarrhalis* 4223. Such isolated and purified about 200 kDa outer membrane protein is substantially free from non-200 kDa outer membrane protein, phospholipids and lipopolysaccharide of Moraxella. The about 200 kDa outer membrane protein is at least about 70 wt % pure, preferably at least about 90 wt % pure, and may be in the form of an aqueous solution thereof.

The present invention also provides a purified and isolated nucleic acid molecule encoding an outer membrane protein of a strain of Moraxella having a molecular mass of about 200 kDa, as determined by SDS-PAGE, or a fragment or an analog of the outer membrane protein. The protein encoded by the nucleic acid molecule may encode a protein containing the amino acid sequence NH$_2$-Asn-Val-Lys-Ser-Val-Ile-Asn-Lys-Glu-Gln-Val-Asn-Asp-Ala-Asn-Lys-x-Gln-Gly-Ile (SEQ ID No: 2) for *Moraxella catarrhalis* strain 4223 or containing the corresponding amino acid sequence from other Moraxella strains.

In a further aspect of the present invention, there is provided a purified and isolated nucleic acid molecule having a sequence selected from the group consisting of (a) the sequence set out in FIG. 6 (SEQ ID No: 1), or the complementary sequence thereto; (b) a sequence encoding an about 200 kDa protein of a strain of Moraxella and containing the amino acid sequence NH$_2$-Asn-Val-Lys-Ser-Val-Ile-Asn-Lys-Glu-Gln-Val-Asn-Asp-Ala-Asn-Lys-x-Gln-Gly-Ile (SEQ ID No: 2), or the complementary sequence thereto; and (c) a nucleotide sequence which hybridizes under stringent conditions to any one of the sequences defined in (a) or (b). The nucleic acid preferably defined in (c) has at least about 90% sequence identity with any one of the sequences defined in (a) or (b).

The nucleic acid molecules provided herein may be included in a vector adapted for transformation of a host.

The nucleic acid molecules provided herein also may be included in an expression vector adapted for transformation of a host along with expression means operatively coupled to the nucleic acid molecule for expression by the host of the about 200 kDa outer membrane protein of a strain of Moraxella or the fragment or the analog of the outer membrane protein. A transformed host containing the expression vector is included within the invention, along with a recombinant outer membrane protein or fragment or analog thereof producible by the transformed host.

The expression means may include a nucleic acid portion encoding a leader sequence for secretion from the host of the outer membrane protein or the fragment or the analog of the outer membrane protein. The expression means may include a nucleic acid portion encoding a lipidation signal for expression from the host of a lipidated form of the outer membrane protein or the fragment or analog thereof.

The present invention further includes a live vector for delivery of the outer membrane protein of the invention or a fragment or analog thereof, comprising a vector containing the nucleic acid molecule provided herein. The live vector may be selected from the group consisting of *E. coli*, Salmonella, BCG, adenovirus, poxvirus, vaccinia and poliovirus.

In accordance with a further aspect of the present invention, there is provided a peptide having no less than six amino acids and no more than 150 amino acids and containing an amino acid sequence corresponding to a portion only of the outer membrane protein of the invention, or a fragment or analog thereof. The peptide may be one having the amino acid sequence $NH_2$-Asn-Val-Lys-Ser-Val-Ile-Asn-Lys-Glu-Gln-Val-Asn-Asp-Ala-Asn-Lys-x-Gln-Gly-Ile (SEQ ID No: 2) for the *Moraxella catarrhalis* 4283 strain or the amino acid sequence for the corresponding peptide for other strains of Moraxella.

The present invention also provides an immunogenic composition comprising an immunoeffective amount of an active component, which may be the outer membrane protein or fragment or analog thereof, nucleic acid molecules, recombinant outer membrane proteins, fragments or analogs thereof, live vectors, and/or peptides as provided herein, along with a pharmaceutically acceptable carrier therefor with the active component producing an immune response when administered to a host, which may be a primate, particularly a human. The immunogenic composition may be formulated as a vaccine for in vivo administration to a host to confer protection against diseases caused by a bacterial pathogen that produces the about 200 kDa outer membrane protein or produces a protein capable of inducing antibodies in the host specifically reactive with the about 200 kDa outer membrane protein. In particular, the bacterial pathogen is a strain of Moraxella, particularly *M. catarrhalis*. The immunogenic composition may be formulated as a microparticle capsule, ISCOM or liposome preparation. The immunogenic composition may be used in combination with a targeting molecule for delivery to specific cells of the immune system as to mucosal surfaces. The immunogenic compositions of the invention (including vaccines) may further comprise at least one other immunogenic or immunostimulating material and the immunostimulating material may be at least one adjuvant. Suitable adjuvants for use in the present invention include, (but are not limited to) aluminum phosphate, aluminum hydroxide, QS21, Quil A, calcium phosphate, calcium hydroxide, zinc hydroxide, a glycolipid analog, and octadecyl ester of an amino acid, a muramyl dipeptide and a lipoprotein. Advantageous combinations of adjuvants are described in copending U.S. patent application Ser. No. 261,194 filed Jun. 16, 1994, assigned to the assignee hereof and the disclosure of which is incorporated herein by reference. The invention further includes an antibody specific for the outer membrane protein provided herein producible by immunizing a host with an immunogenic composition provided herein.

In a further aspect of the invention, there is provided a method of generating an immune response in a host comprising administering thereto an immuno-effective amount of the immunogenic composition as provided herein. The immune response may be a humoral or a cell-mediated immune response. The immune response may provide protection to the host against diseases caused by a bacterial pathogen that produces the about 200 kDa outer membrane protein or produces a protein capable of inducing antibodies in the host specifically reactive with the about 200 kDa outer membrane protein. Hosts in which protection against disease may be conferred include primates including humans.

The present invention provides, in an additional aspect thereof, a method of producing a vaccine comprising administering the immunogenic composition provided herein to a test host to determine an amount and a frequency of administration of the active component to confer protection against disease caused by a bacterial pathogen that produces the about 200 kDa outer membrane protein or produces a protein capable of inducing antibodies in the host specifically reactive with the about 200 kDa outer membrane protein, and formulating the active component in a form suitable for administration to a treated host in accordance with said determined amount and frequency of administration. The treated host may be a human.

A further aspect of the present invention provides a method of determining the presence of nucleic acid encoding an outer membrane protein of a strain of Moraxella having a molecular mass of about 200 kDa, as determined by SDS-PAGE, in a sample, comprising the steps of:

(a) contacting the sample with the nucleic acid molecule provided herein to produce duplexes comprising the nucleic acid molecules and any said nucleic acid molecule encoding the outer membrane protein present in the sample and specifically hybridizable therewith; and (b) determining the production of the duplexes.

In yet a further aspect of the invention, there is provided a method of determining the presence of antibodies specifically reactive with outer membrane protein of a strain of Moraxella having a molecular mass of about 200 kDa, in a sample, comprising the steps of:

(a) contacting the sample with the outer membrane protein as provided herein to produce complexes comprising the outer membrane protein and any said antibodies present in the sample specifically reactive therewith; and (b) determining production of the complexes.

In a further aspect of the invention, there is also provided a method of determining the presence of an outer membrane protein if a strain of Moraxella having a molecular mass of about 200 kDa, in a sample comprising the steps of:

(a) immunizing a subject with the immunogenic composition as provided herein, to produce antibodies specific for the outer membrane protein;

(b) contacting the sample with the antibodies to produce complexes comprising any outer membrane protein present in the sample and said outer membrane protein specific antibodies; and (c) determining production of the complexes.

The outer membrane protein may be part of a *Moraxella catarrhalis* strain.

The present invention provides, in a yet further aspect, a diagnostic kit for determining the presence of nucleic acid encoding an outer membrane protein of a train of Moraxella having a molecular mass of about 200 kDa, as determined by SDS-PAGE, in a sample, comprising:

(a) the nucleic acid molecule as provided herein;

(b) means for contacting the nucleic acid with the sample to produce duplexes comprising the nucleic acid molecule and any said nucleic acid present in the sample and hybridizable with the nucleic acid molecule; and (c) means for determining production of the duplexes.

In yet a further aspect of the invention, there is provided a diagnostic kit for determining the presence of antibodies in a sample specifically reactive with the outer membrane protein of a strain of Moraxella having a molecular mass of about 200 kDa, as determined by SDS-PAGE, comprising:

(a) the outer membrane protein as provided herein;

(b) means for contacting the outer membrane protein with the sample to produce complexes comprising the outer membrane protein and any said antibodies present in the sample; and (c) means for determining production of the complexes.

The invention also provides a diagnostic kit for detecting the presence of an outer membrane protein of a strain of Moraxella having a molecular mass of about 200 kDa, in a sample, comprising:

(a) an antibody specific for the about 200 kDa outer membrane protein as provided herein;

(b) means for contacting the antibody with the sample to produce a complex comprising the outer membrane protein and outer membrane-specific antibody; and (c) means for determining production of the complex.

In a further aspect of the invention, there is provided a method of producing an isolated and purified outer membrane protein of a strain of Moraxella having a molecular mass of about 200 kDa, is determined by SDS-PAGE, comprising the steps of:

(a) providing a cell mass of the Moraxella strain;

(b) disrupting the cell mass to provide a cell lysate;

(c) fractionating the cell lysate to provide a fraction containing the outer membrane protein substantially free from other cell lysate components, and (d) recovering said outer membrane protein.

The bacterial strain may be *Moraxella catarrhalis*. The cell lysate may be fractionated by gel electrophoresis.

In this application, the term "about 200 kDa protein" is used to define a family of outer membrane proteins of *M. catarrhalis* having molecular mass of between about 160 and 230 kDa and includes proteins having variations in their amino acid sequences including those naturally occurring in various strains of Moraxella. The purified and isolated DNA molecules comprising a gene having an open reading frame of the about 200 kDa protein of the present invention also include those encoding functional analogs of the about 200 kDa protein. In this application, a first protein or peptide is a "functional analog" of a second protein if the first protein is immunologically related to and/or has the same function as the second protein or peptide. The functional analog may be, for example, a fragment of the protein or a substitution, addition or deletion mutant thereof.

Advantages of the present invention include:

a method for isolating purified about 200 kDa outer membrane protein of a Moraxella strain that produces the outer membrane protein, including *Moraxella catarrhalis*;

an isolated and purified about 200 kDa outer membrane protein isolatable from a Moraxella strain; and diagnostic kits and immunological reagents for specific identification of Moraxella and hosts infected thereby.

BRIEF DESCRIPTION OF THE DRAWINGS

FIG. 2 shows a comparative analysis of cell proteins from a number of *M. catarrhalis* strains by SDS-PAGE analysis. The identification of the lanes and the sources of the proteins are given in Example 4 below;

FIG. 6 shows the nucleotide sequence (SEQ ID No: 1) of the gene having an open reading frame of the about 200 kDa outer membrane protein of *M. catarrhalis*;

FIG. 7 shows the specific identification of *M. catarrhalis* expressing the about 200 kDa outer membrane protein by guinea pig anti-200 kDa specific antiserum in contrast to other bacteria. Identification of the lanes and bacteria appears below.

GENERAL DESCRIPTION OF INVENTION

Figure 1A:
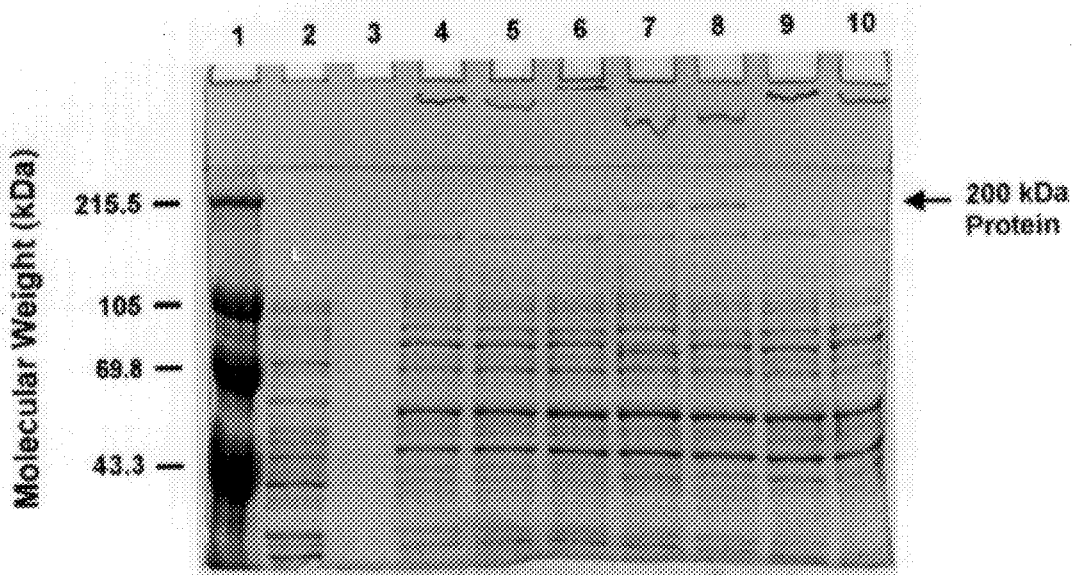
FIGS. 1A and 1B show an analysis of *Moraxella catarrhalis* cell proteins by SDS-PAGE. The identification of the lanes and the sources of the proteins are given in Example 2 below.
Figure 1B:
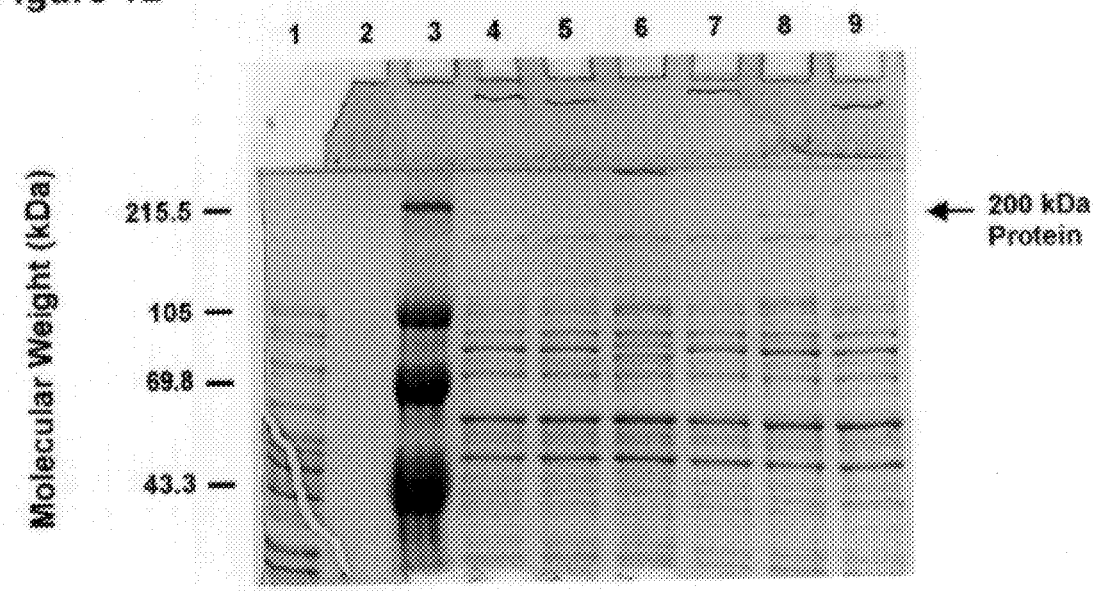
Figure 3:
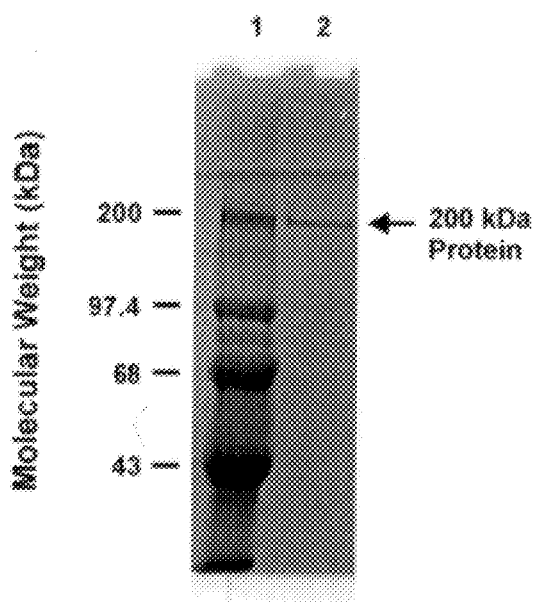
FIG. 3 shows an analysis of isolated and purified about 200 kDa outer membrane protein of *M. catarrhalis* by SDS-PAGE. The identification of the lanes is given in Example 4 below.

Referring to FIG. 1A and 1B and FIG. 2, there is illustrated the separation of a novel outer membrane protein from a variety of strains of *M. catarrhalis* having a molecular mass about 200 kDa. FIG. 3 shows the isolated and purified outer membrane protein.

The purified protein was eluted from the gel and used to raise antibodies in guinea pigs. The antibodies specifically recognize only strains of *M. catarrhalis* which produce the outer membrane protein (Table I below).

Figure 4:
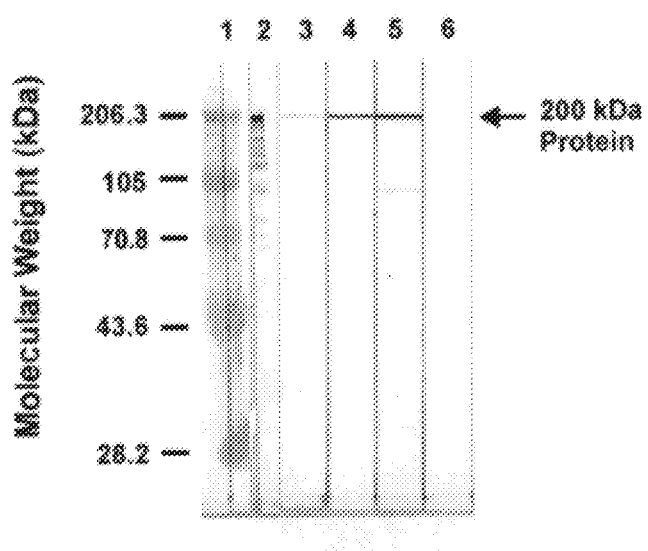
FIG. 4 shows the specific recognition of about 200 kDa outer membrane protein by anti-peptide antiserum. The identification of the lanes and antiserum are given in Example 8 below.

Referring to FIG. 4, there is shown the recognition of the about 200 kDa outer membrane protein by antibodies raised in guinea pigs to a synthesized peptide corresponding to an internal fragment of the about 200 kDa protein. The synthesized peptide had the amino acid sequence $NH_2$-Asn-Val-Lys-Ser-Val-Ile-Asn-Lys-Glu-Gln-Val-Asn-Asp-Ala-Asn-Lys (SEQ ID No: 3).

Figure 5:
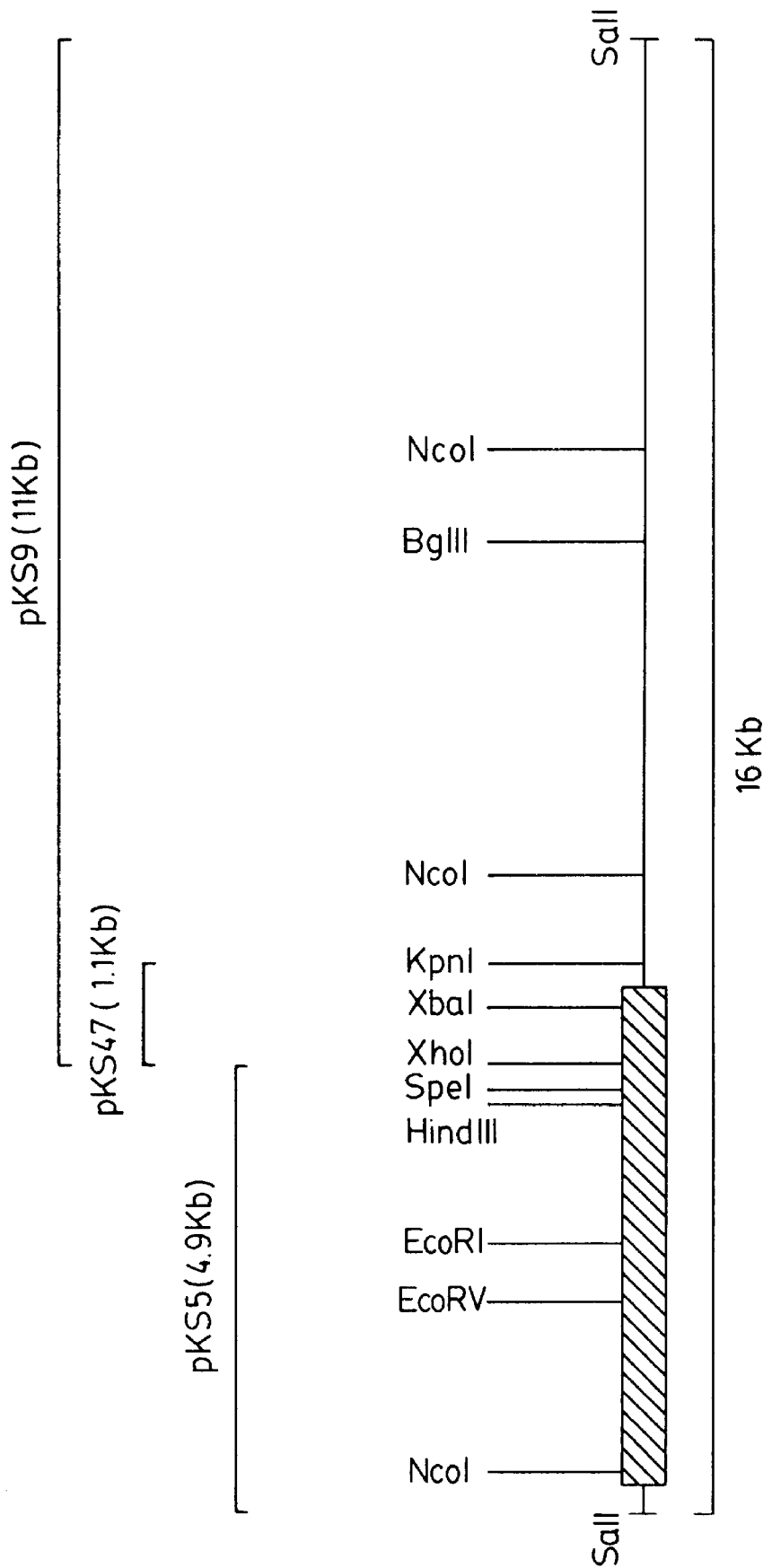
FIG. 5 shows restriction maps of clones containing a gene having an open reading frame of the about 200 kDa outer membrane protein of *M. catarrhalis*. An open reading frame of the about 200 kDa outer membrane protein is indicated by the hatched box.

Referring to FIG. 5, there is shown restriction maps of clones containing a gene having an open reading frame of the about 200 kDa outer membrane protein. The nucleotide sequence (SEQ ID No: 1) of the gene having an open reading frame coding for the about 200 kDa outer membrane protein as shown in FIG. 6.

In one embodiment of the present invention, the isolated and purified about 200 kDa outer membrane protein as provided herein is useful for generating antibodies that can be used to specifically distinguish *M. catarrhalis* from other bacterial pathogens that cause otitis media and other diseases. Thus referring to FIG. 7, there is illustrated an immunoblot showing the specific reactivity of a guinea pig monospecific anti-200 kDa outer membrane protein antiserum produced by immunizing mice with the purified about 200 kDa outer membrane protein as provided herein. The bacterial lysates analyzed were as follows:

| Lane | Bacterium | Source |
|---|---|---|
| 1 | Molecular Weight Standard | |
| 2 | M. catarrhalis 4223 | middle ear fluid |
| 3 | M. catarrhalis RH408 | non-clumping variant of strain 4223 |
| 4 | H. influenzae, MinnA strain | meningitis isolate |
| 5 | non-typable H. influenzae, SB12 strain | otitis media isolate |
| 6 | non-typable H. influenzae, SB33 strain | otitis media isolate |
| 7. | S. pneumoniae type 6 | ATCC 6306 |
| 8. | S. pneumoniae type 14 | ATCC 6314 |
| 9. | P. aeruginosa | |
| 10. | E. coli DH5α | |

The results shown in FIG. 7 clearly show the usefulness of outer membrane-specific antisera as provided herein to distinguish between bacterial pathogens that produce diseases with similar clinical symptoms.

Thus, in accordance with another aspect of the present invention, there is provided a vaccine against Moraxella, comprising an immunogenically-effective amount of the outer membrane protein as provided herein and a physiologically-acceptable carrier therefor. The outer membrane protein provided herein also may be used as a carrier protein for hapten, polysaccharides or peptides to make a conjugate vaccine against antigenic determinants unrelated to the about 200 kDa outer membrane protein.

The about 200 kDa outer membrane protein provided herein is useful as a diagnostic reagent, as an antigen for the generation of anti-outer membrane protein antibodies, or as an antigen for vaccination against the diseases caused by species of Moraxella for detecting infection by Moraxella.

In additional embodiments of the present invention, the about 200 kDa outer membrane protein as provided herein may be used as a carrier molecule to prepare chimeric molecules and conjugate vaccines (including glycoconjugates) against pathogenic bacteria, including encapsulated bacteria. Thus, for example, glycoconjugates of the present invention may be used to confer protection against disease and infection caused by any bacteria having polysaccharide antigens including lipooligosaccharides (LOS) and polyribosylphosphate (PRP). Such bacterial pathogens may include, for example, *Haemophilus influenzae, Streptococcus pneumoniae, Escherichia coli, Neisseria meningitides, Salmonella typhi, Streptococcus mutants, Cryptococcus neoformans, Klebsiella, Staphylococcus aureus* and *Pseudomonas aeruginosa*. Particular antigens which can be conjugated to outer membrane protein and methods to achieve such conjugations are described in published PCT application WO 94/12641, assigned to the assignee hereof and the disclosure of which is hereby incorporated by reference thereto.

In another embodiment, the carrier function of the outer membrane protein may be used, for example, to induce immunity toward abnormal polysaccharides of tumor cells, or to produce anti-tumor antibodies that can be conjugated to chemotherapeutic or bioactive agents.

It is clearly apparent to one skilled in the art, that the various embodiments of the present invention have many applications in the fields of vaccination, diagnosis, treatment of Moraxella infections, and in the generation of immunological reagents. A further non-limiting discussion of such uses is further presented below.

1. Vaccine Preparation and Use

Immunogenic compositions, suitable to be used as vaccines, may be prepared from the about 200 kDa outer membrane protein as disclosed herein, which may be purified from the bacteria or which may be produced recombinantly, as well as immunological fragments thereof. The vaccine elicits an immune response in a subject which produces antibodies, including anti-200 kDa outer membrane protein antibodies and antibodies that are opsonizing or bactericidal. Should the vaccinated subject be challenged by Moraxella or other bacteria that produce proteins capable of producing antibodies that specifically recognize 200 kDa outer membrane protein, the antibodies bind to and inactivate the bacterium. Furthermore, opsonizing or bactericidal anti-200 kDa outer membrane protein antibodies may also provide protection by alternative mechanisms.

Immunogenic compositions including vaccines may be prepared as injectables, as liquid solutions or emulsions. The about 200 kDa outer membrane protein may be mixed with pharmaceutically acceptable excipients which are compatible with the about 200 kDa outer membrane protein. Such excipients may include, water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by injection subcutaneously or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose and magnesium carbonate. These compositions can take the form of solutions, suspensions, tablets, pills, capsules, sustained release formulations or powders and contain about 1 to 95% of the about 200 kDa outer membrane protein. The immunogenic preparations and vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the about 200 kDa outer membrane protein. Suitable regimes for initial administration and booster doses are also variable, but may include an initial administration followed by subsequent administrations. The dosage may also depend on the route of administration and will vary according to the size of the host.

The concentration of the about 200 kDa outer membrane antigen in an immunogenic composition according to the invention is in general about 1 to 95. A vaccine which contains antigenic material of only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

Immunogenicity can be significantly improved if the antigens are co-administered with adjuvants, commonly used as 0.05 to 0.1 percent solution in phosphate-buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and, more recently, a HBsAg vaccine has been adjuvanted with alum. While the usefulness of alum is well established for some applications, it has limitations. For example, alum is ineffective for influenza vaccination and inconsistently elicits a cell mediated immune response.

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are emulsified in adjuvants. Many adjuvants are toxic, inducing granulomas, acute and chronic inflammations (Freund's complete adjuvant) FCA, cytolysis (saponins and Pluronic polymers) and pyrogenicity, arthritis and anterior uveitis (LPS and MDP). Although FCA is an excellent adjuvant and widely used in research, it is not licensed for use in human or veterinary vaccines because of its toxicity.

Desirable characteristics of ideal adjuvants include:

(1) lack of toxicity;
(2) ability to stimulate a long-lasting immune response;
(3) simplicity of manufacture and stability in long-term storage;
(4) ability to elicit both CMI and HIR to antigens administered by various routes, if required;
(5) synergy with other adjuvants;
(6) capability of selectively interacting with populations of antigen presenting cells (APC);
(7) ability to specifically elicit appropriate $T_H 1$ or $T^H 2$ cell-specific immune responses; and
(8) ability to selectively increase appropriate antibody isotype levels (for example, IgA) against antigens.

U.S. Pat. No. 4,855,283 granted to Lockhoff et al on Aug. 8, 1989 which is incorporated herein by reference thereto, teaches glycolipid analogues including N-glycosylamides, N-glycosylureas and N-glycosylcarbamates, each of which is substituted in the sugar residue by an amino acid, as immuno-modulators or adjuvants. Thus, Lockhoff et al. (U.S. Pat. No. 4,855,283 and ref. 27) reported that N-glycolipid analogs displaying structural similarities to the naturally-occurring glycolipids, such as glycosphingolipids and glycoglycerolipids, are capable of eliciting strong immune responses in both herpes simplex virus vaccine and pseudorabies virus vaccine. Some glycolipids have been synthesized from long chain-alkylamines and fatty acids that are linked directly with the sugars through the anomeric carbon atom, to mimic the functions of the naturally occurring lipid residues.

U.S. Pat. No. 4,258,029 granted to Moloney, assigned to the assignee hereof and incorporated herein by reference thereto, teaches that octadecyl tyrosine hydrochloride (OTH) functioned as an adjuvant when complexed with tetanus toxoid and formalin inactivated type I, II and III poliomyelitis virus vaccine. Also, Nixon-George et al. (ref. 24), reported that octadecyl esters of aromatic amino acids complexed with a recombinant hepatitis B surface antigen, enhanced the host immune responses against hepatitis B virus.

Lipidation of synthetic peptides has also been used to increase their immunogenicity. Thus, Wiesmuller (ref. 25) describes a peptide with a sequence homologous to a foot-and-mouth disease viral protein coupled to an adjuvant tripalmityl-S-glyceryl-cysteinylserylserine, being a synthetic analogue of the N-terminal part of the lipoprotein from Gram negative bacteria. Furthermore, Deres et al. (ref. 26) reported in vivo priming of virus-specific cytotoxic T lymphocytes with synthetic lipopeptide vaccine which comprised of modified synthetic peptides derived from influenza virus nucleoprotein by linkage to a lipopeptide, N-palmityl-S-[2,3-bis(palmitylxy)-(2RS)-propyl-[R]-cysteine (TPC).

2. Immunoassays

The about 200 kDa outer membrane protein of the present invention is useful as an immunogen for the generation of anti-200 kDa outer membrane protein antibodies, as an antigen in immunoassays including enzyme-linked immunosorbent assays (ELISA), RIAs and other non-enzyme linked antibody binding assays or procedures known in the art for the detection of anti-bacterial, anti-Moraxella, and anti-200 kDa outer membrane protein antibodies. In ELISA assays, the about 200 kDa outer membrane protein is immobilized onto a selected surface, for example, a surface capable of binding proteins such as the wells of a polystyrene microtiter plate. After washing to remove incompletely adsorbed about 200 kDa outer membrane protein, a nonspecific protein such as a solution of bovine serum albumin (BSA) that is known to be antigenically neutral with regard to the test sample may be bound to the selected surface. This allows for blocking of nonspecific adsorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody) formation. This may include diluting the sample with diluents, such as solutions of BSA, bovine gamma globulin (BGG) and/or phosphate buffered saline (PBS)/Tween. The sample is then allowed to incubate for from 2 to 4 hours, at temperatures such as of the order of about 20° to 37° C. Following incubation, the sample-contacted surface is washed to remove non-immunocomplexed material. The washing procedure may include washing with a solution, such as PBS/Tween or a borate buffer. Following formation of specific immunocomplexes between the test sample and the bound about 200 kDa outer membrane protein, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity such as an enzymatic activity that will generate, for example, a colour development upon incubating with an appropriate chromogenic substrate. Quantification may then be achieved by measuring the degree of colour generation using, for example, a visible spectrophotometer.

BIOLOGICAL MATERIALS

Certain plasmids that contain portions of the gene having the open reading frame of the gene coding for the about 200 kDa outer membrane protein of *M. catarrhalis* strain 4223 that are described and referred to herein have been deposited with the America Type Culture Collection (ATCC) located at 12301 Parklawn Drive, Rockville, Md., 20852, U.S.A., pursuant to the Budapest Treaty and prior to the filing of this application. The identification of the respective portions of the gene and their molecular size are contained in FIG. 5.

Samples of the deposited plasmids will become available to the public upon grant of a patent based upon this United States patent application. The invention described and claimed herein is not to be limited in scope by plasmids deposited, since the deposited embodiment is intended only as an illustration of the invention. Any equivalent or similar plasmids that encode similar or equivalent antigens as described in this application are within the scope of the invention.

| Plasmid | ATCC Designation | Date Deposited |
|---------|------------------|----------------|
| pKS47   | 97,111           | April 7, 1995  |
| PKS5    | 97,110           | April 7, 1995  |
| pKS9    | 97,114           | April 18, 1995 |

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, and immunology used but not explicitly described in this disclosure and these Examples are amply reported in the scientific literature and are well within the ability of those skilled in the art.

Example 1

This Example illustrates the generation of a non-clumping strain (RH408) of *M. catarrhalis*.

*M. catarrhalis* strain 4223, a clumping strain (a common property of Moraxella strains), was inoculated into several flasks containing 20 mL of brain heat infusion (BHI) broth, and the cultures were incubated with shaking (170 rpm) overnight at 37° C. Five mL of each overnight culture were transferred to five individual 1-mL tubes, and were left sitting undisturbed at room temperature for 3 to 8 hours, to allow bacteria to sediment. One hundred µL of the cleared upper phase of each culture medium were used to inoculate 25 mL of BHI broth and cultures were incubated overnight at 37° C., as described above. This passaging was repeated six times, using 25 µL of cleared medium to inoculate 25 mL of BHI for each overnight culture. Non-clumping bacterial cultures were identified by measuring the absorbency $A_{578}$ at intervals over a 3 hour time period, in order to compare the sedimentation rates of the passaged strains to that of the original *M. catarrhalis* strain 4223 culture. Non-clumping mutants, including *M. catarrhalis* RH408, did not aggregate during the three hour time period. On BHI agar plates, strain RH408 had a colony morphology typical for all non-clumping strains. Strain RH408 was previously deposited at the ATCC under the Budapest Treaty on Dec. 13, 1994 with Accession No. 55637.

Example 2

This Example illustrates the identification of the above 200 kDa outer membrane protein of *Moraxella catarrhalis*.

*M. catarrhalis* strains 4223, RH408, 5191, 8185, M2, M5, ATCC 25240, 3, 56, 135, 585 were grown in brain heart infusion (BHI) broth. The culture was incubated overnight with aeration at 37° C.

*M. catarrhalis* cells were sonicated and the total protein was determined using the BCA assay system (Pierce, Rockford, Ill.). Ten µg of total protein were mixed with the SDS-PAGE sample buffer containing 0.3M Tris-HCl (pH 8.0), 50% glycerol, 10% SDS, 20% α-mercaptoethanol and 0.01% bromophenol blue, boiled for 5 minutes and loaded on each lane of SDS-PAGE gel (0.75 mm thick, 7.5% acrylamide). The gels were run at 200 V for 1 hour. Proteins were visualized by staining gels with a solution containing 0.13% Commassie brilliant blue R, 10% acetic acid and 45% methanol. Excess stain was removed with a destaining solution of 5% ethanol and 7.5% acetic acid.

The various Moraxella proteins separated by this procedure are shown in FIGS. 1A and 1B. The *M. catarrhalis* strains tested were as follows:

| FIG. 1A | | |
|---------|---|---|
| Lane | Bacterial Strain | Source |
| 1. | Molecular Weight Standards | |
| 2. | *E. coli* | |
| 3. | No sample | |
| 4. | *M. catarrhalis* 4223 | middle ear fluid |
| 5 | *M. catarrhalis* RH408 | non-clumping variant of 4223 |
| 6. | *M. catarrhalis* 5191 | middle ear fluid |
| 7. | *M. catarrhalis* 818S | nasopharynx |
| 8. | *M. catarrhalis* M2 | sputum |
| 9. | *M. catarrhalis* M5 | sputum |
| 10. | *M. catarrhalis* 25240 | ATCC 25240 |

FIG. IB

| Lane | Bacterial Strain | Source |
|---|---|---|
| 1. | E. coli | |
| 2. | No sample | |
| 3. | Molecular Weight Size Markers | |
| 4. | M. catarrhalis 4223 | middle ear fluid |
| 5 | M. catarrhalis RH408 | non-clumping variant of 4223 |
| 6. | M. catarrhalis 3 | sputum |
| 7. | M. catarrhalis 56 | sputum |
| 8. | M. catarrhalis 135 | middle ear fluid |
| 9. | M. catarrhalis 585 | Blood |

The about 200 kDa outer membrane protein was clearly seen in all otitis media strains (M. catarrhalis 4223, 5191, 135), one isolate from nasopharynx (8185), and in one isolate from sputum (M2). However, the about 200 kDa protein was not detected in three isolates from sputum (3, 56 and M5) and in one strain with unknown origin (ATCC 25240). A very narrow band was found in an isolate from blood of a bacteremia patient (585) and this band was recognized by an anti-200 kDa specific guinea pig serum on an immunoblot. Strain RH408 is a non-clumping spontaneous mutant isolated from strain 4223 (see Example 1) and was found to not express the about 200 kDa protein.

Example 3

This Example illustrates the detection of antibodies specific for the about 200 kDa outer membrane protein in a serum obtained from a convalescent patient having recovered from otitis media due to M. catarrhalis.

After separation by SDS-PAGE, bacterial proteins were transferred from acrylamide gels to prepared PVDF (polyvinylidene fluoride; Millipore) membranes at a constant voltage of 70 V for 1.5 h in a buffer system consisting of 3 g Tris, 14,4 g glycine and 200 ml methanol per liter at 4° C. Membranes with transferred proteins were blocked with Blocking Reagent (from Boehringer Mannheim) diluted in TBS (0.1M Tris, 0.15M Nacl) at room temperature for 30 min. Blots were exposed to convalescent antiserum diluted 1:500 in Blocking Reagent/TBS with 0.1% Tween 20 for 2 hours at room temperature. This patient had otitis media and the M. catarrhalis strain isolated from the patient's ear fluid was M. catarrhalis CJ7. Blots were then washed 2 times in Blocking Reagent/TBS with Tween at 15 min per wash. The reporter conjugate, horseradish peroxidase (HRP) conjugated to protein G, was diluted 1:4000 with Blocking Reagent/TBS with Tween and used to immerse the washed membranes for 30 min at room temperature. Blots were washed twice as above, followed by a TBS wash. Bound antibodies were detected using the Lumi-Glo (Kirkegaard and Perry) chemiluminescent detection system as described by the manufacturer. Treated blots were exposed to X-ray film. Antibodies were detected in this convalescent serum that reacted with the about 200 kDa outer membrane protein of M. catarrhalis CJ7. These results indicate that the about 200 kDa outer membrane protein is an immunogenic protein of M. catarrhalis to which an immune response is elicited during a natural infection by M. catarrhalis.

Example 4

This Example illustrates the isolation and purification of the about 200 kDa outer membrane protein.

M. catarrhalis 4223 cells were harvested by centrifugation at 2,000 rpm for 10 min and frozen. The frozen cells were thawed, resuspended in 20 mM sodium phosphate buffer (pH 7.2) and sonicated until the cells were disrupted. The frozen-thawed cells were also lysed in 20 mM Tris buffer (pH 8) containing 4% SDS and 0.2 mM EDTA by boiling for 5 min to produce a cell lysate. The cell sonicates and cell lysates were suspended in a SDS-polyacrylamide gel electrophoresis (SDS-PAGE) sample buffer, boiled for 5 min and separated by SDS-PAGE on a gel (1.5 mm thick, 7.5% acrylamide). The estimated position of about 200 kDa protein on the gel was cut out and the protein extracted from the gel by electroelution using the same buffer as the SDS-PAGE running buffer. The isolated about 200 kDa outer membrane protein was shown to be a homogeneous, single band by SDS-PAGE as seen in FIG. 3. The samples analyzed in FIG. 3 are as follows:

| Lane | Sample |
|---|---|
| 1. | Molecular Weight Size Markers |
| 2. | Isolated and purified 200 kDa membrane protein |

The isolated and purified 200 kDa outer membrane protein of M. catarrhalis shown in FIG. 3 has a purity of at least 70%. Purified about 200 kDa outer membrane protein preparations of at least 95% could be readily achieved.

When gels were run longer, they showed heterogeneity in the apparent molecular masses of the about 200 kDa outer membrane protein in different strains of M. catarrhalis (FIG. 2). In FIG. 2 the strains analyzed were as follows:

| Lane | Strain | Source |
|---|---|---|
| 1. | Molecular Weight Size Markers | |
| 2. | M. catarrhalis H04 | middle ear fluid |
| 3 | M. catarrhalis H12 | middle ear fluid |
| 4. | M. catarrhalis P034 | middle ear fluid |
| 5. | M. catarrhalis PO51 | middle ear fluid |
| 6. | M. catarrhalis E-07 | middle ear fluid |
| 7. | M. catarrhalis E-22 | middle ear fluid |
| 8. | M. catarrhalis E-23 | middle ear fluid |
| 9. | M. catarrhalis RH 4223 | middle ear fluid |
| 10. | M. catarrhalis RH 408 | Non-clumping variant of 4223 |

The strain H12 (lane 3) was a natural isolate from middle ear fluid, but did not produce the about 200 kDa protein.

There may be at least three different sizes of protein in the about 200 kDa range. However, antibodies raised against the about 200 kDa outer membrane protein from one strain of M. catarrhalis (4223) did recognize all about 200 kDa proteins tested, present in different strains of M. catarrhalis. It is possible, however, that in particular immunogenic compositions, for example, as a vaccine and in particular diagnostic embodiments, that the about 200 kDa outer membrane protein from a variety of M. catarrhalis isolates (including immunogenically diverse isolates) may be required.

Example 5

This Example illustrates the immunization of guinea pigs with purified about 200 kDa protein from M. catarrhalis.

Approximately 30 to 40 μg of the about 200 kDa protein, which was isolated from M. catarrhalis strain 4223 by electroelution, were mixed with Freund's complete adjuvant (FCA) and was subcutaneously injected into guinea pigs. After two weeks, the animals were boosted with about the same amount of the about 200 kDa protein in incomplete Freund's adjuvant (IFA). Two weeks later, blood was collected from the guinea pigs and antisera were obtained.

One antiserum was examined on Western blot for its reactivity with the about 200 kDa protein present in 54 different strains of M. catarrhalis, which were isolated in different geographical locations throughout the world (Canada, U.S. and Finland) (see Table 1 below). The about 200 kDa protein band was clearly recognized by the antiserum in all strains, in which the presence of the about 200 kDa protein band was detected on SDS-PAGE gels stained with Coomassie Blue. These results indicate that common epitopes of the about 200 kDa protein were conserved in all M. catarrhalis strains, which possessed this protein. As stated earlier, this protein is not present in all M. catarrhalis strains, but almost all strains, which were isolated from middle ear fluids from otitis media patients, did possess this protein (Table 1).

Example 6

This Example illustrates the specific recognition of M. catarrhalis strain 4223 with anti-200 kDa protein guinea pig serum by ELISA assay (see Table 2 below).

M. catarrhalis strains 4223, RH408 (200 kDa negative mutant) and H-12 were cultured in 60 mL BHI broth overnight. E. coli strain BL21 (DE3) was cultured in 60 mL Luria-Brtani (LB) broth overnight. The cultures were split into three tubes and centrifuged. M. catarrhalis strain 4223 was centrifuged at 1,500 rpm for 10 minutes, H-12 at 2,000 rpm for 10 minutes, and RH408 and E. coli BL21 (DE3) at 3,000 rpm for 15 minutes. The pellet in one tube was suspended in 20 ml of Dulbecco's phosphate buffered saline (D-PBS) and diluted to 1/500 with coating buffer (0.05M carbonate/bicarbonate buffer) pH 9.6. One hundred μL of the bacteria solution was distributed in each well and incubated for 1 hour at room temperature. One hundred μL of 0.2% glutaraldehyde was added to each well and incubated at room temperature for 10 minutes to fix the cells on the well. The wells were washed with PBS containing 0.1% Tween 20 and 0.1% BSA (washing buffer), and then blocked with PBS containing 0.1% BSA for 30 minutes at room temperature. After washing 5 times for 10 seconds with the washing buffer, serial dilutions of guinea pig antiserum with the washing buffer were added to wells and incubated at room temperature for 60 minutes. After washing, goat anti-guinea pig IgG conjugated with horseradish peroxidase was added to each well at the dilution of 1/20,000. After incubation at room temperature for 60 minutes, the wells were washed and then color reaction was developed using 3,3-5,5-tetramethylbenzidene (TMB) and hydrogen peroxide.

The ELISA plate wells were also coated with sonicates containing 10 μg/mL of total proteins in the coating buffer, blocked without the fixation process and then assayed as described above.

The results shown in Table 2 indicate that the 200 kDa outer membrane protein specific guinea pig antiserum specifically recognizes strains of M. catarrhalis which produce the about 200 kDa protein. The ability of the antiserum to recognize whole cells indicates that the protein is present on the surface of the bacterial cells.

Example 7

This Example describes the determination of an internal amino acid sequence of the 200 kDa outer membrane protein.

The about 200 kDa outer membrane protein was isolated from M. catarrhalis 4223 as described above. The protein was subjected to CNBr degradation, the proteolytic digests subjected to SDS-PAGE and transferred onto PVDF membrane. A peptide band migrating at a position corresponding to approximately 40 kDa was cut out from the membrane and its N-terminal amino acid sequence was determined. In another experiment, the CNBr degradation products of the about 200 kDa protein were subjected to a direct determination of N-terminal amino acid sequencing without separating by SDS-PAGE. Both analyses gave an identical, N-terminal sequence of 20 amino acids with one unidentified amino acid at the 17th position. The internal sequence of the 200 kDa outer membrane protein was:

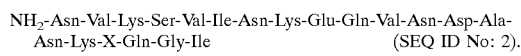
NH$_2$-Asn-Val-Lys-Ser-Val-Ile-Asn-Lys-Glu-Gln-Val-Asn-Asp-Ala-Asn-Lys-X-Gln-Gly-Ile (SEQ ID No: 2).

Example 8

This Example describes the immunization of guinea pigs with a peptide corresponding to an internal fragment of the about 200 kDa outer membrane protein and the analysis of the antiserum generated.

Based upon the determination of the amino acid sequence of an internal fragment of the about 200 kDa outer membrane protein, a 16 amino acid long peptide of sequence:

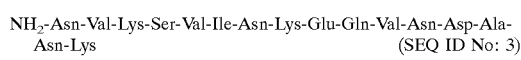
NH$_2$-Asn-Val-Lys-Ser-Val-Ile-Asn-Lys-Glu-Gln-Val-Asn-Asp-Ala-Asn-Lys (SEQ ID No: 3)

was synthesized by standard procedure. This 16-mer peptide was conjugated to KLH using Imject Maleimide Activated KLH (Pierce, Rockford, Ill.) and approximately 500 μg of the conjugate was injected into guinea pigs using the same immunization and boosting schedule as described above. The guinea pig serum raised against the 16-mer internal amino acid sequence (SEQ ID No: 3) was examined by immunoblot analysis and found to specifically recognize 200 kDa outer membrane protein in cell sonicates of M. catarrhalis 4223. The results are shown in FIG. 4 and indicate that the anti-peptide guinea pig antiserum specifically recognizes the 200 kDa protein of M. catarrhalis 4223. The samples analyzed in FIG. 4 were as follows:

| Lane | Sample | Antiserum |
|---|---|---|
| 1. | Molecular Weight Markers | |
| 2. | Purified 200 kDa outer membrane protein | Anti-200 kDa protein |
| 3. | M. catarrhalis cell sonicate | Anti-peptide 1:5000 |
| 4 | M. catarrhalis cell sonicate | Anti-peptide 1:1000 |
| 5. | M. catarrhalis cell sonicate | Anti-peptide 1:500 |
| 6. | M. catarrhalis cell sonicate | Pre-immune serum |

The results obtained confirm that the peptide corresponding to SEQ ID Nos: 2 and 3 are derived from the 200 kDa outer membrane protein.

Example 9

This Example describes the preparation of a M. catarrhalis library.

Chromosomal DNA was isolated as follows:

M. catarrhalis cell pellet was resuspended in 20 mL Tris-EDTA (TE) buffer, pH 7.5. Pronase (final concentration 500 μg/mL) and SDS (final concentration 1%) were added and the suspension was incubated in a 37° C. water bath for 2 hours. DNA was isolated by sequential extractions with phenol (1 time), phenol-chloroform (1:1, 2 times), and chloroform-isoamyl alcohol (24:1, 1 time). Extracted DNA was dialyzed against 1M NaCl at 4° C. for 4 hours. This was followed by dialysis against TE buffer, pH 7.5, at 4° C. for 48 hours (3 buffer changes). DNA was ethanol precipitated from the dialysate. Large size DNA was collected by spooling on a glass rod. Air dried DNA was dissolved in 3 mL water. Small scale Sau3A (New England BioLabs) restriction digests of chromosomal DNA (final volume 10 μl) were done to establish conditions required to obtain maximal amounts of chromosomal DNA with a size range of 15–23 kb. Large scale digests were prepared once the optimal digestion conditions were defined. The large scale digests consisted of 50 μl chromosomal DNA (290 μg/mL), 33 μL water, 10 μL Sau3A buffer (New England BioLabs), 1 μL BSA (10 mg/ml, New England BioLabs) and 6.3 μL Sau3A (0.04 U/μL), and were incubated at 37° C. for 15 minutes. Reactions were stopped with the addition of 10 μL 10× loading buffer (100 mM Tris-HCl pH 8, 10 mM EDTA, 0.1% bromophenol blue, 50% glycerol). Digested DNA was applied to 0.5% agarose gels (prepared in Tris-acetate-EDTA (TAE)) and separated according to size at 50 V for 6 hours. The region of the gel encompassing DNA of size 15–23 kb was cut from the gel and placed in dialysis tubing (BRL) with 3 mL TAE. DNA was electroeluted from the gel slice overnight at a field strength of 1 V/cm. Electroeluted DNA in TAE was extracted once with phenol, once with phenol-chloroform (1:1), and finally precipitated with ethanol. The dried DNA pellet was dissolved in 5 μL water. Size-fractionated chromosomal DNA was ligated with BamHI cut EMBL3 arms (Promega) using T4 DNA ligase in a final volume of 9 μL. The entire ligation reaction was packaged into phage λ using a commercially purchased packaging kit following the manufacturer's (Amersham) protocol.

The packaged DNA library was amplified on solid medium. This was accomplished by incubating 0.1 ml E. coli strain NM539 plating cells (cells suspended in 10 mM MgSO$_4$) with 15–25 μL of the packaged DNA library at 37° C. for 15 minutes. Bacteria with adsorbed phage were plated onto BBL plates (10 g BBL trypticase peptone, 5 g NaCl and 15 g agar per liter) using 3 mL of BBL top-agarose (same as BBL plates except agar replaced with 0.6% agarose) and plates were incubated overnight at 37° C. Phage were eluted from the top-agarose by adding 3 mL SM buffer (50 mM Tris-HCl, pH 7.5, 8 mM MgSO$_4$, 100 mM NaCl, 0.01% gelatin) to the plates and leaving them at 4° C. for 7 hours. SM buffer containing phage was collected from the plates, transferred to a screwcap tube and stored at 4° C. over chloroform.

Example 10

This Example describes the cloning on a gene encoding the M. catarrhalis 200 kDa outer membrane protein.

The M. catarrhalis genomic library in phage lambda EMBL3 was screened using an anti-200 kDa protein guinea pig antiserum. A lambda phage clone 8II (FIG. 5), which expressed as about 200 kDa protein, was confirmed by immunoblotting of the phage lysate using the about 200 kDa outer membrane-specific antiserum.

Plate lysate cultures of this recombinant phage were prepared. The DNA was extracted from the plate lysates using a Wizard Lambda Preps DNA Purification System (Promega Corp, Madison, Wis.) according to the manufacturer's instructions. This phage clone carried a DNA insert of about 16 kb in size (the restriction map for which is in FIG. 5). The phage DNA was digested with a mixture of two restriction enzymes, SalI and XhoI, and separated by agarose gel electrophoresis. Two DNA bands, approximately 5 kb and 11 kb in size, respectively, were cut out from the gel and extracted using a Geneclean kit (BIO 101 Inc., LaJolla, Calif.) according to a manufacturer's instruction.

The smaller 5 kb fragment was ligated into a plasmid vector, pBluescript II SK± (Stratagene Cloning Systems, LaJolla, Calif.), which was previously digested with SalI and XhoI, to produce plasmid pKS5. The larger 11 kb fragment was ligated into a plasmid vector, pSP72 (Promega Corp., Madison, Wis.), to produce plasmid pKS9. Both ligated plasmids were used to transform E. coli, strain DH5α.

The lambda phage DNA was also digested with a mixture of XhoI and KpnI and the approximately 1.2 kb fragment was isolated after agarose gel separation as described above. This 1.2 kb fragment was ligated into a plasmid vector, pGEM-7Zf(+) (Promega Corp., Madison, Wis.), to produce plasmid pKS47. Restriction maps of the lambda and plasmid clones are shown in FIG. 5.

Example 11

This Example describes the sequencing of the gene having an open reading frame of the gene coding for the about 200 kDa outer membrane protein of M. catarrhalis.

The gene encoding the about 200 kDa outer membrane protein was sequenced by an Applied Biosystems sequencer. The one strand of the insert in the plasmid pKS5, was sequenced after construction of a nested set of deletions using a Erase-a-Base system (Promega Corp., Madison, Wis.). The plasmid pKS5 was first digested with XhoI and KpnI, treated with exonuclease III to generate a nested set of deletions in the insert and then recircularized according to the manufacturer's instructions. E. coli DH5α was transformed with a series of plasmids with deletions generated in this way. Plasmids were isolated from the transformants using a Quiagen midi plasmid isolation kit (Qiagen) and the size of plasmids examined by agarose gel electrophoresis after restriction enzyme digestion. The inserts of the plasmids with deletions were sequenced using a bacteriophage T7 promoter sequence as a primer.

Based upon the sequence, nucleotide primers were synthesized. Using the synthetic nucleotide primers, sequence gaps, which were not sequenced by the Erase-a Base system, were determined.

The sequence of the insert in plasmid pKS47 was determined from both ends using synthetic nucleotide primers. The nucleotide sequence of the gene has an open reading frame of the gene coding for the about 200 kDa outer membrane protein of M. catarrhalis as shown in FIG. 6 (SEQ ID No: 1). This sequence included a nucleotide sequence:

5'-AATGTCAAATCAGTCATTAACAAAGAA-
CAAGTAAATGATGCCAATAAAAAGCAA
GGCATC-3'  (SEQ ID No: 4)

which encodes the internal amino acid sequence of the about 200 kDa outer membrane protein (SEQ ID No: 2) determined above. This result confirms that the cloned gene has an open reading frame of the gene coding for the about 200 kDa outer membrane protein of M. catarrhalis.

SUMMARY OF THE DISCLOSURE

In summary of the disclosure, the present invention provides an isolated and purified outer membrane protein of a Moraxella strain, particularly M. catarrhalis, having a molecular weight of about 200 kDa as well as isolated and purified DNA molecules encoding the outer membrane protein. The invention also provides peptides corresponding to portions of the outer membrane protein. The protein, DNA sequences, recombinant proteins derived therefrom and peptides are useful for diagnosis, immunization and the generation of diagnostic and immunological reagents. Modifications are possible within the scope of this invention.

TABLE I

Presence of about 200 kDa outer membrane protein in various isolates of *Moraxella catarrhalis*

| Type of Clinical Isolate | Number of isolates Examined | Number of isolates[1.] containing the 200 kDa outer membrane protein |
| --- | --- | --- |
| Otitis Media | 37 | 36 |
| Sputum/Expectoration/Bronchial Secretion | 13 | 6 |
| Blood | 2 | 2 |
| Nasopharynx | 1 | 1 |
| Unknown | 1 | 0 |

[1.]The presence of the about 200 kDa outer membrane protein was determined by immunoblot analysis using a monospecific guinea pig anti-200 kDa protein antiserum.

TABLE II

Detection of about 200 kDa outer membrane protein of *M. catarrhalis* by the monospecific anti-200 kDa outer membrane guinea pig antiserum

| Strain | Sample | Reciprocal Reactive Titre |
| --- | --- | --- |
| 4223 | Whole cells not fixed | 800 |
| RH408 | Whole cells not fixed | <200 |
| H12 | Whole cells not fixed | <200 |
| *E. coli* BL21 | Whole cells not fixed | <200 |
| 4223 | | 3200 |
| RH408 | | 200 |
| H12 | | <200 |
| *E. coli* BL21 | | <200 |
| 4223 | Sonicate | 12,800 |
| RH408 | Sonicate | 800 |
| H12 | Sonicate | 800 |
| *E. coli* BL21 | Sonicate | 200 |

REFERENCES

1. Van Hare, G. F., P. A. Shurin, C. D. Marchant, N. A. Cartelli, C. E. Johnson, D. Fulton, S. Carlin, and C. H. Kim. Acute otitis media caused by *Branhamella catarrhalis*: biology and therapy. Rev. Infect. Dis. 9:16–27.
2. Chapman, A. J., D. M. Musher, S. Jonsson, J. E. Clarridge, and R. J. Wallace. 1985. Development of bactericidal antibody during *Branhamella catarrhalis* infection. J. Infect. Dis. 151:878–882.
3. Hager, H., A. Verghese, S. Alvarez, and S. L. Berk. 1987. *Branhamella catarrhalis* respiratory infections. Rev. Infect. Dis. 9:1140–1149.
4. McLeod, D. T., F. Ahmad, M. J. Croughan, and M. A. Calder. 1986. Bronchopulmonary infection due to *M. catarrhalis*. Clinical features and therapeutic response. Drugs 31(Suppl.3):109–112.
5. Nicotra, B., M. Rivera, J. I. Luman, and R. J. Wallace. 1986. *Branhamella catarrhalis* as a lower respiratory tract pathogen in patients with chronic lung disease. Arch. Intern. Med. 146:890–893.
6. Ninane, G., J. Joly, and M. Kraytman. 1978. Bronchopulmonary infection due to *Branhamella catarrhalis* 11 cases assessed by transtracheal puncture. Br. Med. Jr. 1:276–278.
7. Srinivasan, G., M. J. Raff, W. C. Templeton, S. J. Givens, R. C. Graves, and J. C. Mel. 1981. *Branhamella catarrhalis* pneumonia. Report of two cases and review of the literature. Am. Rev. Respir. Dis. 123:553–555.
8. West, M., S. L. Berk, and J. K. Smith. 1982. *Branhamella catarrhalis* pneumonia. South. Med. J. 75:1021–1023.
9. Brorson, J.-E., A. Axelsson, and S. E. Holm. 1976. Studies on *Branhamella catarrhalis* (*Neisseria catarrhalis*) with special reference to maxillary sinusitis. Scan. J. Infect. Dis. 8:151–155.
10. Evans, F. O., Jr., J. B. Sydnor, W. E. C. Moore, G. R. Moore, J. L. Manwaring, A. H. Brill, R. T. Jackson, S. Hanna, J. S. Skaar, L. V. Holdeman, G. S. Fitz-Hugh, M. A. Sande, and J. M. Gwaltney, Jr. 1975. Sinmaitis of the maxillary antrum. N. Engl. J. Med. 293:735–739.
11. Tinkelman, D. G., and H. J. Silk. 1989. Clinical and bacteriologic features of chronic sinusitis in children. Am. J. Dis. Child. 143:938–942.
12. Wald, E. R., C. Byers, N. Guerra, M. Casselbrant, and D. Beste. 1989. Subacute sinusitis in children. J. Pediatr. 115:28–32.
13. Wald, E. R., G. J. Milmoe, A. Bowen, J. Ledesma-Medina, N. Salamon, and C. D. Bluestone. 1981. Acute maxillary sinusitis in children. N. Engl. J. Med. 304:749–754.
14. Christensen, J. J., and B. Bruun. 1985. Bacteremia caused by a beta-lactamase producing strain of *Branhamella catarrhalis*. Acta. Pathol. Microbiol. Immunol. Scand. Sect.B 93:273–275.
15. Craig, D. B., and P. A. Wehrle. 1983. *Branhamella catarrhalis* septic arthritis. J. Rheumatol. 10:985–986.
16. Gray, L. D., R. E. Van Scoy, J. P. Anhalt, and P. K. W. Yu. 1989. Wound infection caused by *Branhamella catarrhalis*. J. Clin. Microbiol. 27:818–820.
17. Guthrie, R., K. Bakenhaster, R. Nelson, and R. Woskobnick. 1988. *Branhamella catarrhalis* sepsis: a case report and review of the literature. J. Infect. Dis. 158:907–908.
18. Hiroshi, S., E. J. Anaissie, N. Khardori, and G. P. Bodey. 1988. *Branhamella catarrhalis* septicemia in patients with leukemia. Cancer 61:2315–2317.
19. O'Neill, J. H., and P. W. Mathieson. 1987. Meningitis due to *Branhamella catarrhalis*. Aust. N. Z. J. Med. 17:241–242.
20. Murphy, T. F. 1989. The surface of *Branhamella catarrhalis*: a systematic approach to the surface antigens of an emerging pathogen. Pediatr. Infect. Dis. J. 8:S75–S77.
21. Klingman, K. L., and T. F. Murphy. 1994. Purification and characterization of a high-molecular-weight outer membrane protein of *Moraxella* (*Branhamella*) *catarrhalis*. Infect. Immun. 62:1150–1155.
22. Helminen, M. E., I. Maciver, J. L. Latimer, J. Klesney-Tait, L. D. Cope, M. Paris, G. H. McCracken, Jr., and E. J. Hansen. 1994. A large, antigenically conserved protein on the surface of *Moraxella catarrhalis* is a target for protective antibodies. J. Infect. Dis. 170:867–872.
23. Panezutti H., O. James, E. J. Hanson, Y. Choi, R. E. Harkness, M. H. Klein and P. Chong, 1993. Identification of surface-exposed B-cell epitopes recognized by *Haemophilus influenzae* type b P1 specific monoclonal antibodies. Infec. Immun. 61: 1867–1872.
24. Nixon-George et al. (1990), J. Immunology 144:4798–4802.
25. Wiesmuller (1989), Vaccine 8:29–33.
26. Deres et al. (1989), Nature 342:561.
27. Lockhoff, O. Glycolipids as Immmunomodulators: Synthesis and Properties. 1991. Chem. Int. Ed. Engl. 30:1611–1620.

What we claim is:

1. A purified and isolated nucleic acid molecule encoding an outer membrane protein of a strain of Moraxella having a molecular mass of about 200 kDA, as determined by SDS-PAGE, or an immunogenic fragment of the outer membrane protein containing any one of SEQ ID NOS: 1–3.

2. The nucleic acid molecule of claim 1, wherein the strain of Moraxella is a strain of *Moraxella catarrhalis.*

3. The nucleic acid molecule of claim 2, wherein the strain is *Moraxella catarrhalis* 4223.

4. The nucleic acid molecule of claim 1, wherein the encoded protein contains the amino acid sequence $NH_2$-Asn-Val-Lys-Ser-Val-Ile-Asn-Lys-Glu-Gln-Val-Asn-Asp-Ala-Asn-Lys-x-Gln-Gly-Ile (SEQ ID No: 2) for *Moraxella catarrhalis* strain 4223 or contains said amino acid sequence from other Moraxella strains.

5. A purified and isolated nucleic acid molecule having a nucleotide sequence selected from the group consisting of:

(a) the nucleotide sequence set out in FIGS. 6A to 6F (SEQ ID NO:1), or the complementary sequence thereto;

(b) a nucleotide sequence encoding a 200 kDa protein of a strain of Moraxella and containing the amino acid sequence $NH_2$-Asn-Val-Lys-Ser-Val-Ile-Asn-Lys-Glu-Gln-Val-Asn-Asp-Ala-Asn-Lys-x-Gln-Gly-Ile (SEQ ID NO:2), or the complementary sequence thereto; and (c) a nucleotide sequence encoding a 200 kDa protein of a strain of Moraxella which hybridizes under highly stringent conditions to either of the complementary sequences defined in (a) or (b).

6. The nucleic acid molecule of claim 5, wherein the nucleotide sequence defined in (c) has at least about 90% sequence identity with any one of the sequences defined in (a) or (b).

7. A vector adapted for transformation of a host comprising a nucleic acid molecule having a nucleotide sequence selected from the group consisting of:

(a) the nucleotide sequence set out in FIGS. 6A to 6F (SEQ ID NO:1), or the complementary sequence thereto;

(b) a nucleotide sequence encoding a 200 kDa protein of a strain of Moraxella and containing the amino acid sequence NH$_2$-Asn-Val-Lys-Ser-Val-Ile-Asn-Lys-Glu-Gln-Val-Asn-Asp-Ala-Asn-Lys-x-Gln-Gly-Ile (SEQ ID NO:2), and (c) a nucleotide sequence encoding a 200 kDa protein of a strain of Moraxella which hybridizes under highly stringent conditions to either of the complementary sequences defined in (a) or (b).

8. An expression vector adapted for transformation of a host comprising a nucleic acid molecule having a nucleotide sequence selected from the group consisting of:

(a) the nucleotide sequence set out in FIGS. 6A to 6F (SEQ ID NO:1), or the complementary sequence thereto;

(b) a nucleotide sequence encoding a 200 kDa protein of a strain of Moraxella and containing the amino acid sequence NH$_2$-Asn-Val-Lys-Ser-Val-Ile-Asn-Lys-Glu-Gln-Val-Asn-Asp-Ala-Asn-Lys-x-Gln-Gly-Ile (SEQ ID NO:2), and (c) a nucleotide sequence encoding a 200 kDa protein of a strain of Moraxella which hybridizes under highly stringent conditions to either of the complementary sequences defined in (a) or (b); and expression means operatively coupled to the nucleic acid molecule for expression by the host of an outer membrane protein of a strain of Moraxella having a molecular mass of about 200 kDa, as determined by SDS-PAGE.

9. The expression vector of claim 8, wherein the expression means includes a nucleic acid portion encoding a leader sequence for secretion from the host of the outer membrane protein or the fragment.

10. The expression vector of claim 8, wherein the expression means includes a nucleic acid portion encoding a lipidation signal for expression from the host of a lipidated form of the outer membrane protein.

11. A transformed host containing an expression vector as claimed in claim 8.

12. A live vector for delivery of an outer membrane protein of a strain of Moraxella having a molecular weight of about 200 kDa to a host, comprising a vector containing a nucleic acid molecule having a nucleotide sequence selected from the group consisting of:

(a) the nucleotide sequence set out in FIGS. 6A to 6F (SEQ ID NO:1), or the complementary sequence thereto;

(b) a nucleotide sequence encoding a 200 kDa protein of a strain of Moraxella and containing the amino acid sequence NH$_2$-Asn-Val-Lys-Ser-Val-Ile-Asn-Lys-Glu-Gln-Val-Asn-Asp-Ala-Asn-Lys-x-Gln-Gly-Ile (SEQ ID NO:2), and (c) a nucleotide sequence encoding a 200 kDa protein of a strain of Moraxella which hybridizes under highly stringent conditions to either of the complementary sequences defined in (a) or (b).

13. The live vector of claim 12, wherein the vector is selected from the group consisting of *E. coli*, Salonella, BCG, adenovirus, poxvirus, vaccinia and poliovirus.

* * * * *

UNITED STATES PATENT AND TRADEMARK OFFICE
CERTIFICATE OF CORRECTION

PATENT NO.   : 5,808,024
DATED        : September 15, 1998
INVENTOR(S)  : Sasaki et al.

It is certified that error appears in the above-identified patent and that said Letters Patent is hereby corrected as shown below:

<u>Title page,</u>
Item [73], please insert -- Assignee, Item [73], Connaught Laboratories Limited --.

<u>Column 27,</u>
Line 53, "SEQ ID NOS: 1 TO 3" should be -- SEQ ID NOS: 2 AND 3 --.

Signed and Sealed this

Fifteenth Day of October, 2002

*Attest:*

*Attesting Officer*

JAMES E. ROGAN
*Director of the United States Patent and Trademark Office*

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
(A) LENGTH: 6973 base pairs
(B) TYPE: nucleic acid
(C) STRANDEDNESS: single
(D) TOPOLOGY: linear (xi) SEQUENCE DESCRIPTION: SEQ ID NO:1:

```
CCATGGATAT GGGCAGGTGT GCTCGCCTGC CGTATGATGG CGATGACACC CCATTTGCCC      60
CATATCTGTA CGATTTGACA TGTGATATGA TTTAACATGT GACATGATTT AACATTGTTT     120
AATACTGTTG CCATCATTAC CATAATTTAG TAACGCATTT AGTAACGCAT TTGTAAAAAT     180
CATTGCGCCC CTTTATGTGT ATCATATGAA TAGAATATTA TGATTGTATC TGATTATTGT     240
ATCAGAATGG TGATGCTATA TGATGATGCC TACGAGTTGA TTTGGGTTAA TCACTCTATG     300
ATTTGATATA TTTTGAAACT AATCTATTGA CTTAAATCAC CATATGGTTA TAATTTAGCA     360
TAATGGTAGG CTTTTTGTAA AAATCACATC GCAATATTGT TCTACTGTTA CTACCATGCT     420
TGAATGACGA TCCCAATCAC CAGATTCATT CAAGTGATGT GTTTGTATAC GCACCATTTA     480
CCCTAATTAT TTCAATCAAA TGCCTATGTC AGCATGTATC ATTTTTTAA GGTAAACCAC      540
CATGAATCAC ATCTATAAAG TCATCTTTAA CAAAGCCACA GGCACATTTA TGGCAGTGGC     600
AGAGTACGCC AAATCCCACA GCACGGGGGG GGGGTAGCTG TGCTACAGGG CAAGTTGGCA     660
GTGTATGCAC TCTGAGCTTT GCCCGTATTG CCGCGCTCGC TGTCCTCGTG ATCGGTGCAA     720
CGCTCAGTGG CAGTGCTTAT GCTCAAAAAA AAGATACCAA ACATATCGCA ATTGGTGAAC     780
AAAACCAGCC AAGACGCTCA GGCACTGCCA AGGCGGACGG TGATCGAGCC ATTGCTATTG     840
GTGAAAATGC TAACGCACAG GGCGGTCAAG CCATCGCCAT CGGTAGTAGT AATAAAACTG     900
TCAATGGAAG CAGTTTGGAT AAGATAGGTA CCGATGCTAC GGGTCAAGAG TCCATCGCCA     960
TCGGTGGTGA TGTAAAGGCT AGTGGTGATG CCTCGATTGC CATCGGTAGT GATGACTTAC    1020
ATTTGCTTGA TCAGCATGGT AATCCTAAAC ATCCGAAAGG TACTCTGATT AACGATCTTA    1080
TTAACGGCCA TGCAGTATTA AAAGAAATAC GAAGCTCAAA GGATAATGAT GTAAAATATA    1140
GACGCACAAC CGCAAGCGGA CACGCCAGTA CTGCAGTGGG AGCCATGTCA TATGCACAGG    1200
GTCATTTTTC CAACGCCTTT GGTACACGGG CAACAGCTAA AAGTGCCTAT TCCTTGGCAG    1260
TGGGTCTTGC CGCCACAGCC GAGGGCCAAT CTACAATCGC TATTGGTTCT GATGCAACAT    1320
CTAGCTCGTT GGGAGCGATA GCCCTTGGTG CAGGTACTCG TGCTCAGCTA CAGGGCAGTA    1380
TTGCCCTAGG TCAAGGTTCT GTTGTCACTC AGAGTGATAA TAATTCTAGA CCGGCCTATA    1440
CACCAAATAC CCAGGCACTA GACCCCAAGT TTCAAGCCAC CAATAATACG AAGGCGGGTC    1500
CACTTTCCAT TGGTAGTAAC TCTATCAAAC GTAAAATCAT CAATGTCGGT GCAGGTGTTA    1560
ATAAAACCGA TGCGGTCAAT GTGGCACAGC TAGAAGCGGT GGTGAAGTGG CTAAGGAGC     1620
GTAGAATTAC TTTTCAGGGT GATGATAACA GTACTGACGT AAAAATAGGT TTGGATAATA    1680
CTTTAACTAT TAAAGGTGGT GCAGAGACCA ACGCATTAAC CGATAATAAT ATCGGTGTGG    1740
TAAAAGAGGC TGATAATAGT GGTCTGAAAG TTAAACTTGC TAAAACTTTA AACAATCTTA    1800
CTGAGGTGAA TACAACTACA TTAAATGCCA CAACCACAGT TAAGGTAGGT AGTAGTAGTA    1860
```

```
GTACTACAGC  TGAATTATTG  AGTGATAGTT  TAACCTTTAC  CCAGCCCAAT  ACAGGCAGTC  1920
AAAGCACAAG  CAAAACCGTC  TATGGCGTTA  ATGGGGTGAA  GTTACTAAT   AATGCAGAAA  1980
CAACAGCAGC  AATCGGCACT  ACTCGTATTA  CCAGAGATAA  AATTGGCTTT  GCTCGAGATG  2040
GTGATGTTGA  TGAAAAACAA  GCACCATATT  TGGATAAAAA  ACAACTTAAA  GTGGGTAGTG  2100
TTGCAATTAC  CATAGACAAT  GGCATTGATG  CAGGTAATAA  AAAGATCAGT  AATCTTGCCA  2160
AAGGTAGCAG  TGCTAACGAT  GCGGTTACCA  TCGAACAGCT  CAAAGCCGCC  AAGCCTACTT  2220
TAAACGCAGG  CGCTGGCATC  AGTGTCACAC  CTACTGAAAT  ATCAGTTGAT  GCTAAGAGTG  2280
GCAATGTTAC  CGCCCCAACT  TACAACATTG  GCGTGAAAAC  CACCGAGCTT  AACAGTGATG  2340
GCACTAGTGA  TAAATTTAGT  GTTAAGGGTA  GTGGTACGAA  CAATAGCTTA  GTTACCGCCG  2400
AACATTTGGC  AAGCTATCTA  AATGAAGTCA  ATCGAACGGC  TGACAGTGCT  CTACAAAGCT  2460
TTACCGTTAA  AGAAGAAGAC  GATGATGACG  CCAACGCTAT  CACCGTGGCT  AAAGATACGA  2520
CAAAAAATGC  CGGCGCAGTC  AGCATCTTAA  AACTCAAAGG  TAAAAACGGT  CTAACGGTTG  2580
CTACCAAAAA  AGATGGTACG  GTTACCTTTG  GGCTTAGCCA  AGATAGCGGT  CTGACCATTG  2640
GCAAAGCAC   CCTAAACAAC  GATGGCTTGA  CTGTTAAAGA  TACCAACGAA  CAAATCCAAG  2700
TCGGTGCTAA  TGGCATTAAA  TTTACTAATG  TGAATGGTAG  TAATCCAGGT  ACTGGCATTG  2760
CAAATACCGC  TCGCATTACC  AGAGATAAAA  TTGGCTTTGC  TGGTTCTGAT  GGTGCAGTTG  2820
ATACAAACAA  ACCTTATCTT  GATCAAGACA  AGCTACAAGT  TGGCAATGTT  AAGATTACCA  2880
ACACTGGCAT  TAACGCAGGT  GGTAAAGCCA  TCACAGGGCT  GTCCCCAACA  CTGCCTAGCA  2940
TTGCCGATCA  AAGTAGCCGC  AACATAGAAC  TGGGCAATAC  AATCCAAGAC  AAAGACAAAT  3000
CCAACGCTGC  CAGCATTAAT  GATATATTAA  ATACAGGCTT  TAACCTAAAA  AATAATAACA  3060
ACCCCATTGA  CTTTGTCTCC  ACTTATGACA  TTGTTGACTT  TGCCAATGGC  AATGCCACCA  3120
CCGCCACAGT  AACCCATGAT  ACCGCTAACA  AAACCAGTAA  AGTGGTATAT  GATGTGAATG  3180
TGGATGATAC  AACCATTCAT  CTAACAGGCA  CTGATGACAA  TAAAAAACTT  GGCGTCAAAA  3240
CCACCAAACT  GAACAAAACA  AGTGCTAATG  GTAATACAGC  AACTAACTTT  AATGTTAACT  3300
CTAGTGATGA  AGATGCCCTT  GTTAACGCCA  AAGACATCGC  CGAAAATCTA  AACACCCTAG  3360
CCAAGGAAAT  TCACACCACC  AAAGGCACAG  CAGACACCGC  CCTACAAACC  TTTACCGTTA  3420
AAAAGGTAGA  TGAAAATAAT  AATGCTGATG  ACGCCAACGC  CATCACCGTG  GGTCAAAAGA  3480
ACGCAAATAA  TCAAGTCAAC  ACCCTAACAC  TCAAAGGTGA  AAACGGTCTT  AATATTAAAA  3540
CCGACAAAAA  TGGTACGGTT  ACCTTTGGCA  TTAACACCAC  AAGCGGTCTT  AAAGCCGGCA  3600
AAAGCACCCT  AAACGACGGT  GGCTTGTCTA  TTAAAAACCC  CACTGGTAGC  GAACAAATCC  3660
AAGTCGGTGC  TGATGGCGTG  AAGTTTGCCA  AGGTTAATAA  TAATGGTGTT  GTAGGTGCTG  3720
GCATTGATGG  CACAACTCGC  ATTACCAGAG  ATGAAATTGG  CTTTACTGGG  ACTAATGGCT  3780
CACTTGATAA  AAGCAAACCC  CACCTAAGCA  AAGACGGCAT  TAACGCAGGT  GGTAAAAAGA  3840
TTACCAACAT  TCAATCAGGT  GAGATTGCCC  AAAACAGCCA  TGATGCTGTG  ACAGGCGGCA  3900
AGATTTATGA  TTTAAAAACC  GAACTTGAAA  ACAAAATCAG  CAGTACTGCC  AAAACAGCAC  3960
AAAACTCATT  ACACGAATTC  TCAGTAGCAG  ATGAACAAGG  TAATAACTTT  ACGGTTAGTA  4020
ACCCTTACTC  CAGTTATGAC  ACCTCAAAGA  CCTCTGATGT  CATCACCTTT  GCAGGTGAAA  4080
ACGGCATTAC  CACCAAGGTA  AATAAGGTG   TGGTGCGTGT  GGGCATTGAC  CAAACCAAAG  4140
GCTTAACCAC  GCCTAAGCTG  ACCGTGGGTA  ATAATAATGG  CAAAGGCATT  GTCATTGACA  4200
GCCAAAATGG  TCAAAATACC  ATCACAGGAC  TAAGCAACAC  TCTAGCTAAT  GTTACCAATG  4260
```

| | | | | | | |
|---|---|---|---|---|---|---|
| ATAAAGGTAG | CGTACGCACC | ACAGAACAGG | GCAATATAAT | CAAAGACGAA | GACAAAACCC | 4320 |
| GTGCCGCCAG | CATTGTTGAT | GTGCTAAGCG | CAGGCTTTAA | CTTGCAAGGC | AATGGTGAAG | 4380 |
| CGGTTGACTT | TGTCTCCACT | TATGACACCG | TCAACTTTGC | CGATGGCAAT | GCCACCACCG | 4440 |
| CTAAGGTGAC | CTATGATGAC | ACAAGCAAAA | CCAGTAAAGT | GGTCTATGAT | GTCAATGTGG | 4500 |
| ATGATACAAC | CATTGAAGTT | AAAGATAAAA | AACTTGGCGT | AAAAACCACC | ACATTGACCA | 4560 |
| GTACTGGCAC | AGGTGCTAAT | AAATTTGCCC | TAAGCAATCA | AGCTACTGGC | GATGCGCTTG | 4620 |
| TCAAGGCCAG | TGATATCGTT | GCTCATCTAA | ACACCTTATC | TGGCGACATC | CAAACTGCCA | 4680 |
| AAGGGGCAAG | CCAAGCGAAC | AACTCAGCAG | GCTATGTGGA | TGCTGATGGC | AATAAGGTCA | 4740 |
| TCTATGACAG | TACCGATAAC | AAGTACTATC | AAGCCAAAAA | TGATGGCACA | GTTGATAAAA | 4800 |
| CCAAAGAAGT | TGCCAAAGAC | AAACTGGTCG | CCCAAGCCCA | AACCCCAGAT | GGCACATTGG | 4860 |
| CTCAAATGAA | TGTCAAATCA | GTCATTAACA | AGAACAAGT | AAATGATGCC | AATAAAAAGC | 4920 |
| AAGGCATCAA | TGAAGACAAC | GCCTTTGTTA | AAGGACTTGA | AAAAGCCGCT | TCTGATAACA | 4980 |
| AAACCAAAAA | CGCCGCAGTA | ACTGTGGGTG | ATTTAAATGC | CGTTGCCCAA | ACACCGCTGA | 5040 |
| CCTTTGCAGG | GGATACAGGC | ACAACGGCTA | AAAACTGGG | CGAGACTTTG | ACCATCAAAG | 5100 |
| GTGGGCAAAC | AGACACCAAT | AAGCTAACCG | ATAATAACAT | CGGTGTGGTA | GCAGGTACTG | 5160 |
| ATGGCTTCAC | TGTCAAACTT | GCCAAAGACC | TAACCAATCT | TAACAGCGTT | AATGCAGGTG | 5220 |
| GCACCAAAAT | TGATGACAAA | GGCGTGTCTT | TTGTAGACTC | AAGCGGTCAA | GCCAAAGCAA | 5280 |
| ACACCCCTGT | GCTAAGTGCC | AATGGGCTGG | ACCTGGGTGG | CAAGGTCATC | AGTAATGTGG | 5340 |
| GCAAAGGCAC | AAAAGATACC | GACGCTGCCA | ATGTACAACA | GTTAAACGAA | GTACGCAACT | 5400 |
| TGTTGGGTCT | TGGTAATGCT | GGTAATGATA | ACGCTGACGG | CAATCAGGTA | AACATTGCCG | 5460 |
| ACATCAAAAA | AGACCCAAAT | TCAGGTTCAT | CATCTAACCG | CACTGTCATC | AAAGCAGGCA | 5520 |
| CGGTACTTGG | CGGTAAAGGT | AATAACGATA | CCGAAAAACT | TGCCACTGGT | GGTATACAAG | 5580 |
| TGGGCGTGGA | TAAAGACGGC | AACGCTAACG | GCGATTTAAG | CAATGTTTGG | GTCAAAACCC | 5640 |
| AAAAAGATGG | CAGCAAAAAA | GCCCTGCTCG | CCACTTATAA | CGCCGCAGGT | CAGACCAACT | 5700 |
| ATTTGACCAA | CAACCCCGCA | GAAGCCATTG | ACAGAATAAA | TGAACAAGGT | ATCCGCTTCT | 5760 |
| TCCATGTCAA | CGATGGCAAT | CAAGAGCCTG | TGGTACAAGG | GCGTAACGGC | ATTGACTCAA | 5820 |
| GTGCCTCAGG | CAAGCACTCA | GTGGCGATAG | GTTTCCAGGC | CAAGGCAGAT | GGTGAAGCCG | 5880 |
| CCGTTGCCAT | AGGCAGACAA | ACCCAAGCAG | GCAACCAATC | CATCGCCATC | GGTGATAACG | 5940 |
| CACAAGCCAC | GGGCGATCAA | TCCATCGCCA | TCGGTACAGG | CAATGTGGTA | GCAGGTAAGC | 6000 |
| ACTCTGGTGC | CATCGGCGAC | CCAAGCACTG | TTAAGGCTGA | TAACAGTTAC | AGTGTGGGTA | 6060 |
| ATAACAACCA | GTTTACCGAT | GCCACTCAAA | CCGATGTCTT | TGGTGTGGGC | AATAACATCA | 6120 |
| CCGTGACCGA | AAGTAACTCG | GTTGCCTTAG | GTTCAAACTC | TGCCATCAGT | GCAGGCACAC | 6180 |
| ACGCAGGCAC | ACAAGCCAAA | AAATCTGACG | GCACAGCAGG | TACAACCACC | ACAGCAGGTG | 6240 |
| CAACCGGTAC | GGTTAAAGGC | TTTGCTGGAC | AAACGGCGGT | TGGTGCGGTC | TCCGTGGGTG | 6300 |
| CCTCAGGTGC | TGAACGCCGT | ATCCAAAATG | TGGCAGCAGG | TGAGGTCAGT | GCCACCAGCA | 6360 |
| CCGATGCGGT | CAATGGTAGC | CAGTTGTACA | AGCCACCCA | AAGCATTGCC | AACGCAACCA | 6420 |
| ATGAGCTTGA | CCATCGTATC | CACCAAAACG | AAAATAAGGC | CAATGCAGGG | ATTTCATCAG | 6480 |
| CGATGGCGAT | GGCGTCCATG | CCACAAGCCT | ACATTCCTGG | CAGATCCATG | GTTACCGGGG | 6540 |
| GTATTGCCAC | CCACAACGGT | CAAGGTGCGG | TGGCAGTGGG | ACTGTCGAAG | CTGTCGGATA | 6600 |
| ATGGTCAATG | GGTATTTAAA | ATCAATGGTT | CAGCCGATAC | CCAAGGCCAT | GTAGGGGCGG | 6660 |

```
CAGTTGGTGC  AGGTTTTCAC  TTTTAAGCCA  TAAATCGCAA  GATTTTACTT  AAAAATCAAT        6720

CTCACCATAG  TTGTATAAAA  CAGCATCAGC  ATCAGTCATA  TTACTGATGC  TGATGTTTTT        6780

TATCACTTAA  ACCATTTTAC  CGCTCAAGTG  ATTCTCTTTC  ACCATGACCA  AATCGCCATT        6840

GATCATAGGT  AAACTTATTG  AGTAAATTTT  ATCAATGTAG  TTGTTAGATA  TGGTTAAAAT        6900

TGTGCCATTG  ACCAAAAAAT  GACCGATTTA  TCCCGAAAAT  TTCTGATTAT  GATCCGTTGA        6960

CCTGCAGGTC  GAC                                                              6973
```

( 2 ) INFORMATION FOR SEQ ID NO:2:

( i ) SEQUENCE CHARACTERISTICS:
( A ) LENGTH: 19 amino acids
( B ) TYPE: amino acid
( C ) STRANDEDNESS: single
( D ) TOPOLOGY: linear ( x i ) SEQUENCE DESCRIPTION: SEQ ID NO:2:

```
Asn Val Lys Ser Val Ile Asn Lys Glu Gln Val Asn Asp Ala Asn Lys
1               5                   10                  15

Gln Gly Ile
```

( 2 ) INFORMATION FOR SEQ ID NO:3:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( x i ) SEQUENCE DESCRIPTION: SEQ ID NO:3:

```
Asn Val Lys Ser Val Ile Asn Lys Glu Gln Val Asn Asp Ala Asn Lys
1               5                   10                  15
```

( 2 ) INFORMATION FOR SEQ ID NO:4:

( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( x i ) SEQUENCE DESCRIPTION: SEQ ID NO:4:

```
AATGTCAAAT CAGTCATTAA CAAAGAACAA GTAAATGATG CCAATAAAAA GCAAGGCATC    60
```